US011685932B2

(12) United States Patent
Hein et al.

(10) Patent No.: US 11,685,932 B2
(45) Date of Patent: Jun. 27, 2023

(54) INDUCIBLE AAV REP GENES

(71) Applicant: Cevec Pharmaceuticals, GmbH, Cologne (DE)

(72) Inventors: Kerstin Hein, Cologne (DE); Nicole Faust, Cologne (DE); Silke Wissing, Cologne (DE)

(73) Assignee: Cevec Pharmaceuticals, GmbH, Cologne (DE)

( * ) Notice: Subject to any disclaimer, the term of this patent is extended or adjusted under 35 U.S.C. 154(b) by 552 days.

(21) Appl. No.: 16/646,741

(22) PCT Filed: Sep. 18, 2018

(86) PCT No.: PCT/EP2018/075158

§ 371 (c)(1),
(2) Date: Mar. 12, 2020

(87) PCT Pub. No.: WO2019/057691

PCT Pub. Date: Mar. 28, 2019

(65) Prior Publication Data

US 2020/0277628 A1 Sep. 3, 2020

(30) Foreign Application Priority Data

Sep. 19, 2017 (EP) .................................... 17001562

(51) Int. Cl.
*C12N 15/86* (2006.01)
*C12N 15/01* (2006.01)
*C12N 15/63* (2006.01)

(52) U.S. Cl.
CPC ............. *C12N 15/86* (2013.01); *C12N 15/01* (2013.01); *C12N 15/63* (2013.01); *C12N 2750/14122* (2013.01); *C12N 2750/14143* (2013.01); *C12N 2750/14152* (2013.01)

(58) Field of Classification Search
CPC ........ C12N 15/86; C12N 15/01; C12N 15/63; C12N 2750/14122; C12N 2750/14143; C12N 2750/14152; C12N 7/00; C12N 2750/14161; C07K 14/005
See application file for complete search history.

(56) References Cited

U.S. PATENT DOCUMENTS

2014/0242671 A1* 8/2014 Grieger .................... C12N 7/00 435/235.1

FOREIGN PATENT DOCUMENTS

WO WO 03/104392 12/2003

OTHER PUBLICATIONS

Chejanovsky N, Carter BJ. Mutagenesis of an AUG codon in the adeno-associated virus rep gene: effects on viral DNA replication. Virology. Nov. 1989;173(1):120-8. (Year: 1989).*

Sitaraman V, Hearing P, Ward CB, Gnatenko DV, Wimmer E, Mueller S, Skiena S, Bahou WF. Computationally designed adeno-associated virus (AAV) Rep 78 is efficiently maintained within an adenovirus vector. Proc Natl Acad Sci USA. Aug. 23, 2011; 108(34):14294-9. Epub Aug. 15, 2011. (Year: 2011).*

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Winkler K, Kramer A, Kuttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Beloukhova MI, Lukashev AN, Volchkov PY, Zamyatnin AA Jr, Deviatkin AA. Robust AAV Genotyping Based on Genetic Distances in Rep Gene That Are Maintained by Ubiquitous Recombination. Viruses. May 13, 2022;14(5):1038. (Year: 2022).*

Chejanovsky et al, Mutagenesis of an AUG codon in the adeno-associated virus rep gene, effects on viral DNA replication, 1989, Virol. vol. 173, pp. 120-128.

Niimi et al, High expression of N-acetylglucosaminetransferase IVa promotes invasion of choriocarcinoma, 2012, Brit. J. Cancer vol. 107, pp. 1969-1977.

Zhang et al, Relations of the type and branch of surface N-glycans to cell adhesion, migration, and integrin expression, 2004, Mole Cell Biol vol. 260, pp. 137-146.

McCarty et al., Sequences required for coordinate induction of adeno-associated virus P19 and P40 proimoters by Rep protein, 1991, Database Biosis Prev199192028340.

Lackner et al, Studies of the mechanism of transactivation of the adeno-associated virus p19 promoter by the Rep protein, 2002, J. Virol, vol. 76, pp. 8225-8235.

Chejanovsky, N. and Carter, B.J., "Mutagenesis of an AUG Codon in the Adeno-Associated Virus rep Gene: Effects on Viral DNA Replication", 9 pages, 1989, Virology 173, pp. 120-128.†

* cited by examiner
† cited by third party

*Primary Examiner* — Rachel B Gill
(74) *Attorney, Agent, or Firm* — HelixIP LLP

(57) ABSTRACT

The present invention relates to host cells comprising a nucleic acid encoding Adeno-associated virus (AAV) Rep proteins Rep78 and Rep68, wherein the internal AAV promoter p19 has been inactivated by one or more mutations that maintain the functionality of said Rep78 and Rep68 proteins. The present invention further relates to respective nucleic acids and vectors comprising the same, as well as respective methods for the production of AAV.

10 Claims, 14 Drawing Sheets

Figure 1:
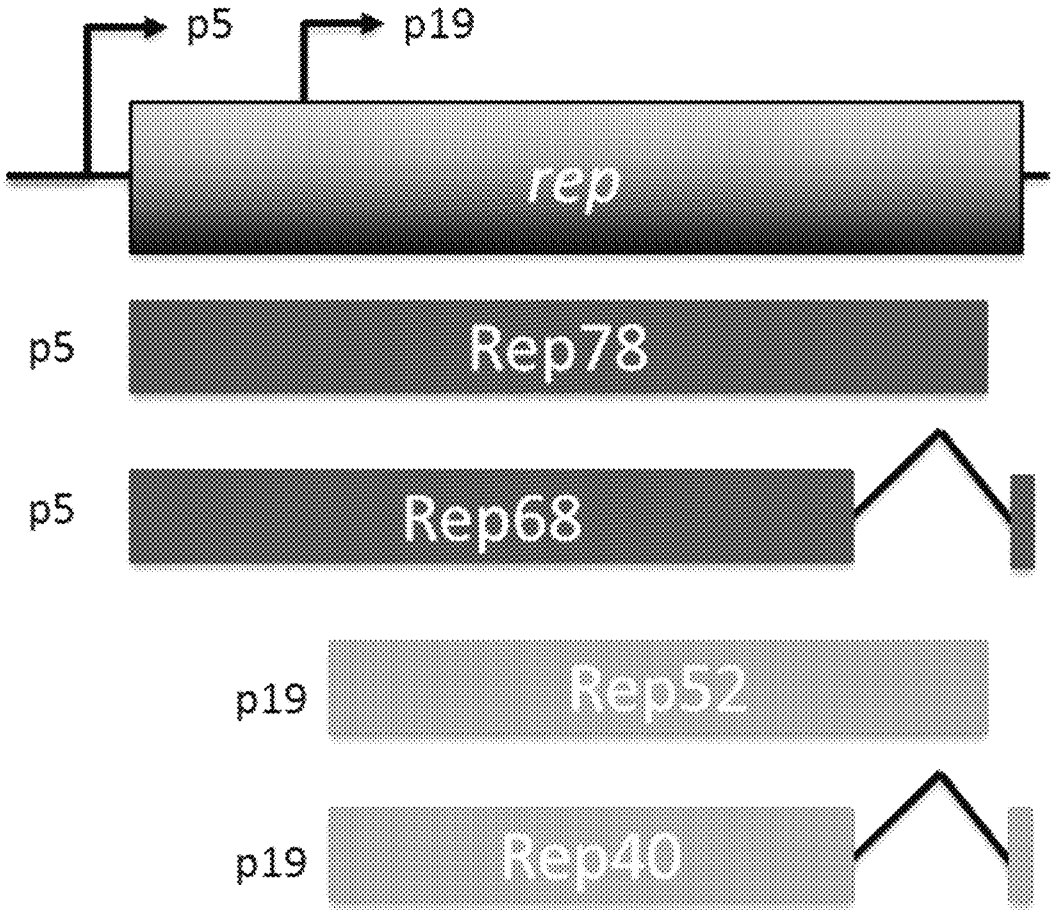

Specification includes a Sequence Listing.

C

D

E

F

A

B

C

D

E

F

A

B

C

INDUCIBLE AAV REP GENES

This application is a is a 371 of PCT/EP2018/075158, having an international filing date of Sep. 18, 2018, which claims the benefit of European Patent Application Serial No. 17001562.2, filed Sep. 19, 2017, the content of which is incorporated by reference in its entirety.

The official copy of the Sequence Listing is submitted concurrently with the specification as an ASCII formatted text file via EFS-Web, with a file name of "CVC007_ST25.txt", a creation date of Feb. 21, 2020, and a size of 89 kilobytes. The Sequence Listing filed via EFS-Web is part of the specification and is incorporated in its entirety by reference herein.

The present invention relates to host cells comprising a nucleic acid encoding Adeno-associated virus (AAV) Rep proteins Rep78 and Rep68, wherein the internal AAV promoter p19 has been inactivated by one or more mutations that maintain the functionality of said Rep78 and Rep68 proteins. The present invention further relates to respective nucleic acids and vectors comprising the same, as well as respective methods for the production of AAV.

Recently there has been a rapid increase in the number of gene therapy trials and products based on Adeno-associated virus (AAV)-derived vectors. Advantages of AAV vectors in gene therapy are a good safety profile, the fact that such vectors are not pathogenic, i.e., are not associated with any disease, the stable expression of transgenes, and the possibility of transducing dividing as well as non-dividing cells.

The production of recombinant AAV inter alia requires the expression of AAV Rep and Cap proteins, usually encoded by the AAV genome, for production of recombinant virus supplied in trans. Further, helper genes must be used which can be derived from different helper viruses, the most common being helper virus genes taken from Adenovirus (AV), such as E1A, E1B, E2A, E4orf6, or VA RNA. Furthermore, a transfer vector containing the gene of interest (GOI) is needed.

Current production systems for AAV rely mostly on the following techniques which, however, have several drawbacks. Transient transfection of AAV rep genes, e.g. using a three-plasmid system comprising a transfer vector containing the gene of interest, a plasmid with adenoviral helper functions, and a plasmid supplying the capsid and replicase functions, lacks scalability, robustness, reproducibility, and entails high costs of GMP-grade DNA. Producer cell lines which are mostly based on HeLa cells still need infection with helper virus, thus requiring extensive purification and costly proof of the absence of helper viruses. Inducible expression of AAV rep genes by way of insertion of a stop cassette into the rep locus downstream of the p19 promoter requires the insertion of an artificial intron that contains a stop signal (e.g. SV40 Poly(A)) flanked by two loxP sites. In addition, cells need the Cre recombinase that recognizes the loxP sites and excises the stop cassette. This has either to be supplied inducibly or by a modified adenoviral vector, requiring the costly proof of the absence of helper virus. Further, Cre-mediated recombination often shows only a low efficiency.

Accordingly, current AAV production systems are limited with respect to scalability, robustness, reproducibility, ease of use and cost efficiency. Thus, a scalable system for the stable production of AAV vectors that does not require transient transfection or helper virus is highly desirable.

Accordingly, the technical problem underlying the present invention is to provide respective host cells, nucleic acids, vectors and methods constituting such a system.

The solution to the above technical problem is achieved by the embodiments characterized in the claims.

In particular, in a first aspect, the present invention relates to a host cell comprising a nucleic acid encoding Adeno-associated virus (AAV) Rep proteins Rep78 and Rep68, wherein the internal AAV promoter p19 has been inactivated by one or more mutations that maintain the functionality of said Rep78 and Rep68 proteins.

In this context, stable producer cell lines for the production of AAV are difficult to generate, as Rep proteins are toxic for cells. The expression of Rep proteins is regulated by E1A that is also necessary for AAV production. In cell lines such as CAP cells, HEK293 cells or Per.C6 cells, E1A is already constitutively expressed. In total, four Rep proteins exist: two long ones (Rep78, Rep68) which are expressed from the p5 promoter, and two short ones (Rep52, Rep40) which are expressed from the internal p19 promoter that is located within the coding region of the long Rep proteins (see FIG. 1 for a schematic overview).

The p5 promoter can be replaced by an inducible promoter but not the internal p19 promoter which is part of the Rep78 and Rep68 coding region. Thus, the generation of packaging/producer cell lines based on cells constitutively expressing E1A is impossible, since this would result in a constitutive expression of toxic levels of Rep52 and Rep40. Other cell lines not constitutively expressing EA1 need inducible E1A or E1A supply, e.g. by infection with Adenovirus, entailing the drawbacks indicated above.

This problem is advantageously solved by the present invention which is based on the inactivation of the internal AAV p19 promoter by mutations which prevent constitutive Rep52 and Rep40 expression while at the same time maintaining the functionality of said Rep78 and Rep68 proteins.

The terms "Adeno-associated virus" and "AAV" as used herein are not limited to particular AAV serotypes. In this context, it should be noted that AAV Rep proteins are highly conserved among the different AAV serotypes. In particular embodiments, the above terms refer to Adeno-associated virus serotype 2 (AAV2).

The term "maintain the functionality of said Rep78 and Rep68 proteins" as used herein refers to the fact that the mutations according to the present invention do not reduce the functional activity of said proteins, or reduce said activity at most by 30%, preferably at most 25%, at most 20%, at most 15%, at most 12.5%, at most 10%, at most 7.5%, at most 5%, at most 4%, at most 3%, at most 2%, or at most 1%.

In preferred embodiments, the one or more mutations according to the present invention are within at least one of the regulatory sites of the p19 promoter, preferably the SP1 −50 region (nucleotides 817 to 829), the TATA −20 region (nucleotides 843 to 849), or the TATA −35 region (nucleotides 830 to 835). Specifically, said one or more mutations can be within the SP1 −50 region, within the TATA −20 region, within the TATA −35 region, within both the SP1 −50 region and the TATA −20 region, within both the SP1 −50 regions and the TATA −35 region, within both the TATA −20 region and the TATA −35 region, or within all three regions, i.e., in the SP1 −50 region, the TATA −20 region, and the TATA −35 region. In particular, it has been shown in the present invention that even mutation of a single nucleotide within one of said regions advantageously leads to significant reduction of Rep52 and Rep40 expression.

In this context, all nucleotide positions as indicated herein refer to the AAV2 complete genome sequence available under GenBank accession number AF043303. The same applies to all amino acid positions. Further, Table 1 below shows an excerpt of the one-letter nucleotide nomenclature according to IUPAC.

TABLE 1

One-letter nucleotide nomenclature according to IUPAC.

| Letter | Nucleotides |
|---|---|
| W | A; T |
| S | C; G |
| M | A; C |
| K | G; T |
| R | A; G |
| Y | C; T |
| B | C; G; T |
| D | A; G; T |
| H | A; C; T |
| V | A; C; G |

In preferred embodiments, the one or more mutations according to the present invention which inactivate the internal p19 promoter are silent mutations, i.e., mutations that do not alter the encoded amino acid.

Preferably, said one or more mutations comprise at least one mutation, selected from the group consisting of mutations 731C>D, 732A>C, 734A>B, 737T>C, 746A>G, 749C>D, 752G>H, 758G>A, 761G>H, 764G>H, 818G>A, 824G>H, 830T>V, 833T>C, 845T>C, 846T>C, 848A>B or 848A>G, 849A>T, 850G>C, and 851C>D.

In cases where said one or more mutations are within the SP1 −50 region of the p19 promoter, said mutations comprise at least one mutation, selected from the group consisting of mutations 818G>A and 824G>H. In cases wherein said one or more mutations are within the TATA −20 region of the p19 promoter, said mutations comprise at least one mutation, selected from the group consisting of mutations 845T>C, 846T>C, 848A>B or 848A>G, and 849A>T. In cases wherein said one or more mutations are within the TATA −35 region of the p19 promoter, said mutations comprise at least one mutation, selected from the group consisting of mutations 830T>V, and 833T>C.

In preferred embodiments, said one or more mutations comprise 2, 3, 4, 5, 6, 7, 8, 9, 10, 11, 12, 13, 14, 15, 16, 17, 18, 19, or all 20 of the above mutations. Accordingly, the host cells of the present invention can comprise a nucleic acid comprising any one, any two, and three, any four, any five, any six, any seven, any eight, any nine, any ten, any eleven, any twelve, any 13, any 14, any 15, any 16, any 17, any 18, any 19, or all 20 of the mutations 731C>D, 732A>C, 734A>B, 737T>C, 746A>G, 749C>D, 752G>H, 758G>A, 761G>H, 764G>H, 818G>A, 824G>H, 830T>V, 833T>C, 845T>C, 846T>C, 848A>B or 848A>G, 849A>T, 850G>C, and 851C>D.

The nucleic acid used in the present invention, encoding Adeno-associated virus (AAV) Rep proteins Rep78 and Rep68, wherein the internal AAV promoter p19 has been inactivated by silent mutations, is preferably a nucleic acid comprising at least one nucleotide sequence, selected from the group consisting of the nucleotide sequences according to SEQ ID NO: 1 to 8, 11 to 14, and 34 to 42. In particularly preferred embodiments, said nucleic acid comprises the nucleotide sequence according to SEQ ID NO: 1, 6, 8, 13, 14, 34 to 39, 41, and 42.

In this context, the term "internal promoter" as used herein indicates the fact that the AAV p19 promoter is located within the coding sequence of Rep78 and Rep68, and forms a part of said coding sequence. Further, the term "inactivated" with respect to the AAV p19 promoter indicates the fact that by way of introducing silent mutations into the AAV p19 promoter region, said promoter has abolished or at least strongly reduced (e.g. reduced by at least 50%, at least 75%, at least 80%, at least 85%, at least 90%, at least 95%, at least 97%, at least 98%, or at least 99%) promoter activity.

The nucleotide sequences according to SEQ ID NOs: 1 to 8, 11 to 14, and 34 to 42 represent the AAV p19 promoter region (nucleotides 651 to 1053 of the AAV2 genome), wherein the mutation patterns indicated in Table 2 below are present.

In preferred embodiments, the nucleic acid used in the present invention, encoding Adeno-associated virus (AAV) Rep proteins Rep78 and Rep68, wherein the internal AAV promoter p19 has been inactivated by silent mutations, is preferably a nucleic acid comprising a nucleotide sequence, selected from the group consisting of the nucleotide sequences according to SEQ ID NOs: 15 to 22, 25 to 28, and 43 to 51. In particularly preferred embodiments, said nucleic acid comprises the nucleotide sequence according to SEQ ID NO: 15, 20, 22, 27, 28, 43 to 48, 50, and 51.

The nucleotide sequences according to SEQ ID NOs: 15 to 22, 25 to 28, and 43 to 51 represent the AAV coding region for the Rep proteins Rep78, Rep68, Rep52 and Rep40 (nucleotides 321 to 2252 of the AAV2 genome), wherein the p19 promoter region (nucleotides 651 to 1053 of the AAV2 genome) has been replaced by the mutated p19 promoter region containing the mutations indicated in Table 2 below.

TABLE 2

Preferred p19 promoter region mutation patterns.

| SEQ ID NO: | Mutation pattern | Mutations |
|---|---|---|
| 1/15 | mut19 | 731C > D; 732A > C; 734A > B; 737T > C; 746A > G; 749C > D; 752G > H; 758G > A; 761G > H; 764G > H; 818G > A; 824G > H; 830T > V; 833T > C; 845T > C; 848A > G; 849A > T; 850G > C; 851C > D |
| 2/16 | mut5 | 845T > C; 848A > G; 849A > T; 850G > C; 851C > D |
| 3/17 | mut1 | 848A > G |
| 4/18 | mut2 | 849A > T; 850G > C |
| 5/19 | mut1-2 | 845T > C |
| 6/20 | mut14 | 731C > D; 732A > C; 734A > B; 737T > C, 746A > G; 749C > D; 752G > H, 758G > A; 761G > H; 764G > H, 818G > A; 824G > H, 830T > V; 833T > C |
| 7/21 | mut10 | 731C > D; 732A > C; 734A > B; 737T > C, 746A > G; 749C > D; 752G > H; 758G > A; 761G > H; 764G > H |
| 8/22 | mut10-2 | 818G > A; 824G > H, 830T > V; 833T > C, 845T > C; 846T > C; 848A > B; 849A > T; 850G > C; 851C > D |
| 11/25 | mut2-3 | 846T > C; 848A > B |
| 12/26 | mut1-3 | 846T > C |
| 13/27 | mut5-2 | 845T > C, 846T > C; 848A > B, 849A > T, 850G > C |
| 14/28 | mut20 | 731C > D; 732A > C; 734A > B; 737T > C, 746A > G; 749C > D; 752G > H, 758G > A; 761G > H; 764G > H, 818G > A; 824G > H, 830T > V; 833T > C, 845T > C, 846T > C; 848A > B, 849A > T, 850G > C, 851C > D |
| 34/43 | L (SP1 -50) | 818G > A; 824G > H |
| 35/44 | M (TATA -20) | 830T > V; 833T > C |
| 36/45 | N (SP1 -50 1) | 818G > A |
| 37/46 | O (SP1 -50 2) | 824G > H |

TABLE 2-continued

Preferred p19 promoter region mutation patterns.

| SEQ ID NO: | Mutation pattern | Mutations |
|---|---|---|
| 38/47 | P (TATA -20 1) | 830T > V |
| 39/48 | Q (TATA -20 2) | 833T > C |
| 40/49 | R (SP1 -50 & TATA -35) | 818G > A; 824G > H; 830T > V; 833T > C |
| 41/50 | S (SP1 -50 & TATA -20) | 818G > A; 824G > H; 845T > C, 846T > C; 848A > B, 849A > T, 850G > C |
| 42/51 | T (TATA -20 & TATA -35) | 830T > V; 833T > C; 845T > C, 846T > C; 848A > B, 849A > T, 850G > C |

In other preferred embodiments, the one or more mutations according to the present invention which inactivate the internal p19 promoter are mutations that result in one or more conservative amino acid exchanges, i.e., amino acid exchanges that change an amino acid to a different amino acid with similar biochemical properties (e.g. regarding charge, hydrophobicity or size). Preferably, said one or more amino acid exchanges are amino acid exchanges occurring within the class of aliphatic amino acids (Gly, Ala, Val, Leu, Ile), within the class of hydroxyl- or sulphur/selenium-containing amino acids (Ser, Cys, Sec, Thr, Met), within the class of basic amino acids (His, Lys, Arg), or within the class of acidic amino acids (Asp, Glu, Asn, Gln).

In particular embodiments, said one or more amino acid exchanges comprise the amino acid exchanges Leu176>Ala and/or Ala168>Gly.

In this respect, the nucleic acid used in the present invention, encoding Adeno-associated virus (AAV) Rep proteins Rep78 and Rep68, wherein the internal AAV promoter p19 has been inactivated by mutations resulting in conservative amino acid exchanges, is preferably a nucleic acid comprising at least one nucleotide sequence, selected from the group consisting of the nucleotide sequences according to SEQ ID NOs: 9 and 10.

In this context, the term "inactivated" with respect to the AAV p19 promoter indicates the fact that by way of introducing mutations resulting in conservative amino acid exchanges into the AAV p19 promoter region, said promoter has abolished or at least strongly reduced (e.g. reduced by at least 50%, at least 75%, at least 80%, at least 85%, at least 90%, at least 95%, at least 97%, at least 98%, or at least 99%) promoter activity.

The nucleotide sequences according to SEQ ID NOs: 9 and 10 represent the AAV p19 promoter region (nucleotides 651 to 1053 of the AAV2 genome), wherein the mutation patterns indicated in Table 3 below are present.

In preferred embodiments, the nucleic acid used in the present invention, encoding Adeno-associated virus (AAV) Rep proteins Rep78 and Rep68, wherein the internal AAV promoter p19 has been inactivated by mutations resulting in conservative amino acid exchanges, is a nucleic acid comprising at least one nucleotide sequence, selected from the group consisting of the nucleotide sequences according to SEQ ID NOs: 23 and 24.

The nucleotide sequences according to SEQ ID NOs: 23 and 24 represent the AAV coding region for the Rep proteins Rep78, Rep68, Rep52 and Rep40 (nucleotides 321 to 2252 of the AAV2 genome), wherein the p19 promoter region (nucleotides 651 to 1053 of the AAV2 genome) has been replaced by the mutated p19 promoter region containing the mutations indicated in Table 3 below.

TABLE 3

Preferred p19 promoter region mutation patterns.

| SEQ ID NO: | Mutation pattern | Mutations | Resulting amino acid exchange |
|---|---|---|---|
| 9/23 | mut3 | 846T > G, 847T > C, 848A > B | Leu176 > Ala |
| 10/24 | mut2-2 | 823C > G, 824G > H | Ala168 > Gly |

The nucleic acid comprised in the host cell of the present invention can further comprise at least one element, selected from the group consisting of inducible promoters, poly(A) regions, selection markers, IRES sequences and enhancing elements. Suitable inducible promoters are not particularly limited and are known in the art, e.g. Tet-inducible promoters such as the third generation TRE3G-promoter. Suitable poly(A) regions are not particularly limited and are known in the art, e.g. the SV40 poly(A) region. Suitable selection markers are not particularly limited and are known in the art, e.g. antibiotic resistance cassettes such as blasticidin or ampicillin resistance cassettes.

The present invention also relates to host cells comprising a nucleic acid having at least 70% sequence identity to a nucleic acid as defined above, provided that the specific mutations defined above are present. In this context, the term "provided that the specific mutations defined above are present" refers to the following situations (i) to (xxiii):

(i) in nucleotide sequences derived from the nucleotide sequences according to SEQ ID NOs: 1 or 15, the mutations 731C>D; 732A>C; 734A>B; 737T>C; 746A>G; 749C>D; 752G>H; 758G>A; 761G>H; 764G>H; 818G>A; 824G>H; 830T>V; 833T>C; 845T>C; 848A>G; 849A>T; 850G>C; and 851C>D are present;

(ii) in nucleotide sequences derived from the nucleotide sequences according to SEQ ID NOs: 2 or 16, the mutations 845T>C; 848A>G; 849A>T; 850G>C; and 851C>D are present;

(iii) in nucleotide sequences derived from the nucleotide sequences according to SEQ ID NOs: 3 or 17, the mutation 848A>G is present;

(iv) in nucleotide sequences derived from the nucleotide sequences according to SEQ ID NOs: 4 or 18, the mutations 849A>T; and 850G>C are present;

(v) in nucleotide sequences derived from the nucleotide sequences according to SEQ ID NOs: 5 or 19, the mutation 845T>C is present;

(vi) in nucleotide sequences derived from the nucleotide sequences according to SEQ ID NOs: 6 or 20, the mutations 731C>D; 732A>C; 734A>B; 737T>C, 746A>G; 749C>D; 752G>H, 758G>A; 761G>H; 764G>H, 818G>A; 824G>H, 830T>V; and 833T>C are present;

(vii) in nucleotide sequences derived from the nucleotide sequences according to SEQ ID NOs: 7 or 21, the mutations 731C>D; 732A>C; 734A>B; 737T>C, 746A>G; 749C>D; 752G>H; 758G>A; 761G>H; and 764G>H are present;

(viii) in nucleotide sequences derived from the nucleotide sequences according to SEQ ID NOs: 8 or 22, the mutations 818G>A; 824G>H, 830T>V; 833T>C, 845T>C; 846T>C; 848A>B; 849A>T; 850G>C; and 851C>D are present;

(ix) in nucleotide sequences derived from the nucleotide sequences according to SEQ ID NOs: 9 or 23, the mutations 846T>G, 847T>C, and 848A>B are present;

(x) in nucleotide sequences derived from the nucleotide sequences according to SEQ ID NOs: 10 or 24, the mutations 823C>G, and 824G>H are present;

(xi) in nucleotide sequences derived from the nucleotide sequences according to SEQ ID NOs: 11 or 25, the mutations 846T>C; and 848A>B are present;

(xii) in nucleotide sequences derived from the nucleotide sequences according to SEQ ID NOs: 12 or 26, the mutation 846T>C is present;

(xiii) in nucleotide sequences derived from the nucleotide sequences according to SEQ ID NOs: 13 or 27, the mutations 845T>C, 846T>C; 848A>B, 849A>T, and 850G>C are present;

(xiv) in nucleotide sequences derived from the nucleotide sequences according to SEQ ID NOs: 14 or 28, the mutations 731C>D; 732A>C; 734A>B; 737T>C, 746A>G; 749C>D; 752G>H, 758G>A; 761G>H; 764G>H, 818G>A; 824G>H, 830T>V; 833T>C, 845T>C, 846T>C; 848A>B, 849A>T, 850G>C, and 851C>D are present;

(xv) in nucleotide sequences derived from the nucleotide sequences according to SEQ ID NOs: 34 or 43, the mutations 818G>A and 824G>H are present;

(xvi) in nucleotide sequences derived from the nucleotide sequences according to SEQ ID NOs: 35 or 44, the mutations 830T>V and 833T>C are present;

(xvii) in nucleotide sequences derived from the nucleotide sequences according to SEQ ID NOs: 36 or 45, the mutation 818G>A is present;

(xviii) in nucleotide sequences derived from the nucleotide sequences according to SEQ ID NOs: 37 or 46, the mutation 824G>H is present;

(xix) in nucleotide sequences derived from the nucleotide sequences according to SEQ ID NOs: 38 or 47, the mutation 830T>V is present;

(xx) in nucleotide sequences derived from the nucleotide sequences according to SEQ ID NOs: 39 or 48, the mutation 833T>C is present;

(xxi) in nucleotide sequences derived from the nucleotide sequences according to SEQ ID NOs: 40 or 49, the mutations 818G>A; 824G>H; 830T>V; and 833T>C are present;

(xxii) in nucleotide sequences derived from the nucleotide sequences according to SEQ ID NOs: 41 or 50, the mutations 818G>A; 824G>H; 845T>C, 846T>C; 848A>B, 849A>T, and 850G>C are present; and (xxiii) in nucleotide sequences derived from the nucleotide sequences according to SEQ ID NOs: 42 or 51, the mutations 830T>V, 833T>C, 845T>C, 846T>C; 848A>B, 849A>T, and 850G>C are present.

Preferably, said nucleic acids have at least 70%, 72%, 74%, 76%, 78%, 80%, 82%, 84%, 86%, 88%, 90%, 91%, 92%, 93%, 94%, 95%, 95.5%, 96%, 96.5%, 97%, 97.5%, 98%, 98.2%, 98.4%, 98.6%, 98.8%, 99%, 99.1%, 99.2%, 99.3%, 99.4%, 99.5%, 99.6%, 99.7%, 99.8%, or 99.9% sequence identity to a nucleic acid as defined above. In particular embodiments, such nucleic acids have 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 nucleotide deletions, insertions or replacements (exchanges).

Respective nucleic acids having a defined sequence identity to a nucleic acid as defined above or having specific nucleotide deletions, insertions or replacements with respect to a nucleic acid as defined above exclude any nucleic acids having any kind of frameshift mutation, as well as any nucleic acids encoding non-functional Rep78 and Rep68 proteins, i.e., said nucleic acids still encode functional Rep78 and Rep68 proteins.

In preferred embodiments, the nucleic acid comprised in the host cells of the present invention is stably integrated into the host cell genome. In other preferred embodiments, the nucleic acid comprised in the host cells of the present invention is comprised in a vector, i.e., is part of a vector. Said vector is preferably a vector selected from the group consisting of plasmid vectors, viral vectors, cosmid vectors, and artificial chromosome vectors. Preferably said vector is an expression vector.

According to the present invention, the internal AAV p19 promoter is inactivated by introduction of silent mutations or mutations resulting in conservative amino acid exchanges. In this manner, a nucleic acid encoding Rep78 and Rep68 can be placed under the control of an inducible promoter, wherein no constitutive expression of Rep52 and Rep40 occurs. However, since production of AAV requires all four Rep proteins, an additional nucleic acid encoding Rep52 and Rep40 can be placed under the control of the same promoter, an identical promoter or a different promoter. Thus, in specific embodiments, the host cell of the present invention further comprises a nucleic acid encoding AAV Rep proteins Rep52 and Rep40 under the control of an inducible promoter. This nucleic acid can be part of the vector as defined above, or of the nucleic acid encoding Rep78 and Rep68.

Host cells suitable for the present invention are not particularly limited and are known in the art. Preferably, said host cells display constitutive E1A expression. In preferred embodiments, said host cells are CAP cells, HEK293 cells or Per.C6 cells, i.e., are derived from said cell lines.

Methods for generating the host cells of the present invention, i.e., methods for the introduction of the nucleic acids of the present invention into suitable host cells, are not particularly limited and are known in the art. The same applies to methods for the generation of the nucleic acids and vectors of the present invention.

In a second aspect, the present invention relates to the nucleic acids and vectors as defined above.

In a third aspect, the present invention relates to a method for the production of Adeno-associated virus (AAV), comprising the step of recombinantly expressing AAV Rep proteins Rep78 and Rep68 in a host cell according to the present invention.

Respective methods for generating the necessary nucleic acids, vectors, and/or host cells, as well as respective expression methods, are not particularly limited and are known in the art.

Preferably, the method of the present invention further comprises the step of recombinantly expressing AAV Rep proteins Rep52 and Rep40 in said host cells.

As used herein, the term "comprising"/"comprises" expressly includes the terms "consisting essentially of"/"consists essentially of" and "consisting of"/"consists of", i.e., all of said terms are interchangeable with each other.

According to the present invention, host cells are provided that can express AAV Rep proteins Rep78 and Rep68 without constitutive expression of Rep52 and Rep40. This is achieved by providing nucleic acids wherein the internal AAV p19 promoter region is inactivated by introducing specific mutations.

Promoters are activated by binding of specific transcription factors and basal transcription complex; these factors recognize specific binding sites within the promoter region that have previously been described for the p19 promoter.

Mutating these binding sites abolishes activation of the promoter. Since the integrity of the long Rep proteins has to be maintained, mutations are chosen that do alter the nucleotide sequence but within the genetic code encode the same amino acid and, therefore, result in formation of the same protein (silent mutations), or mutations are chosen that alter the nucleotide sequence resulting in conservative amino acid exchanges.

After introducing the above mutations, it is possible to separate the expression units for long and short Rep proteins: The expression cassette for the long Rep proteins contains the mutated p19 promoter with said mutations. The isolated expression unit for the short Rep proteins starts downstream of the p19 promoter with the start codon. Expression of both expression units can then be placed under regulation of an inducible promoter (as e.g. Tet inducible promoters). Based on this, a stable packaging/producer cell line can be generated.

The host cells, nucleic acids, vectors, and methods of the present invention represent a system for the production of AAV that is advantageously characterized by superior reproducibility, ensuring consistent quality, scalability, and cost efficiency, which does not need the use of helper virus.

The figures show:

FIG. 1:

Schematic overview of the rep locus.

FIG. 2:

Schematic overview of expression construct for inducible Rep proteins.

Figure 3:
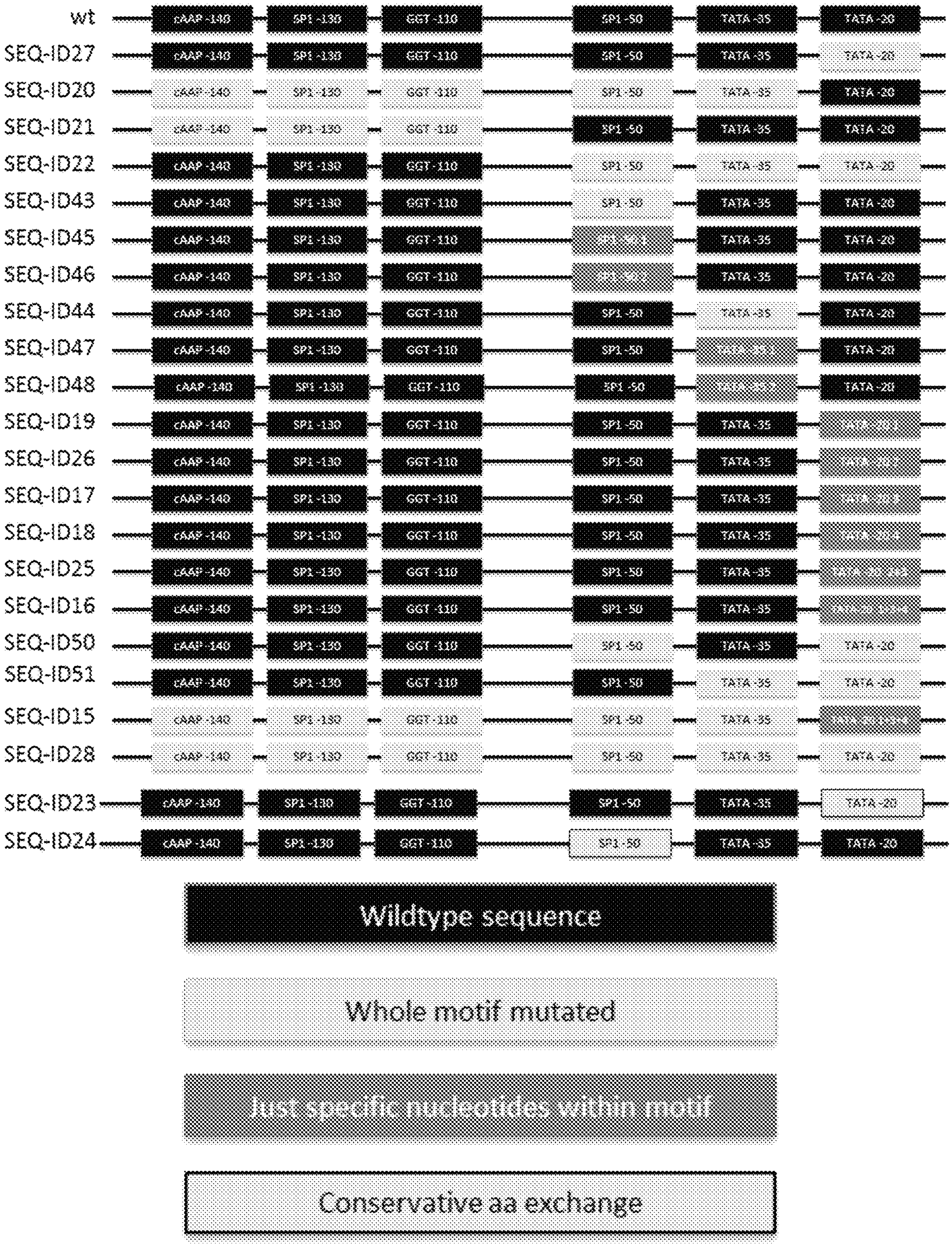
Figure 4A:
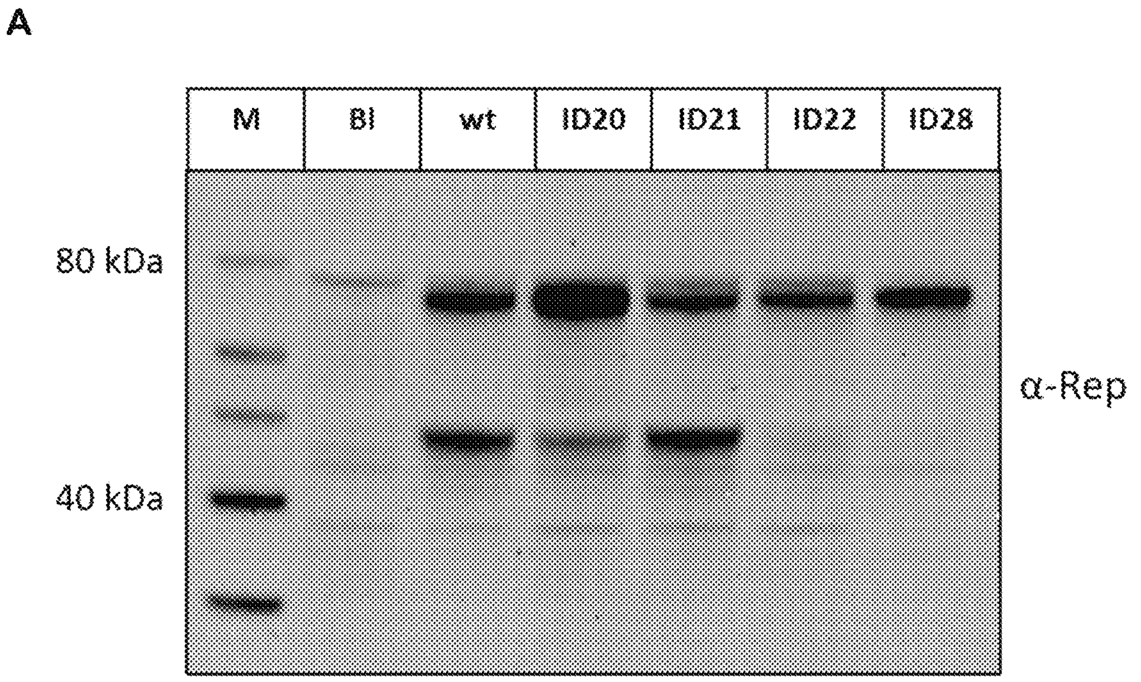
Figure 4B:
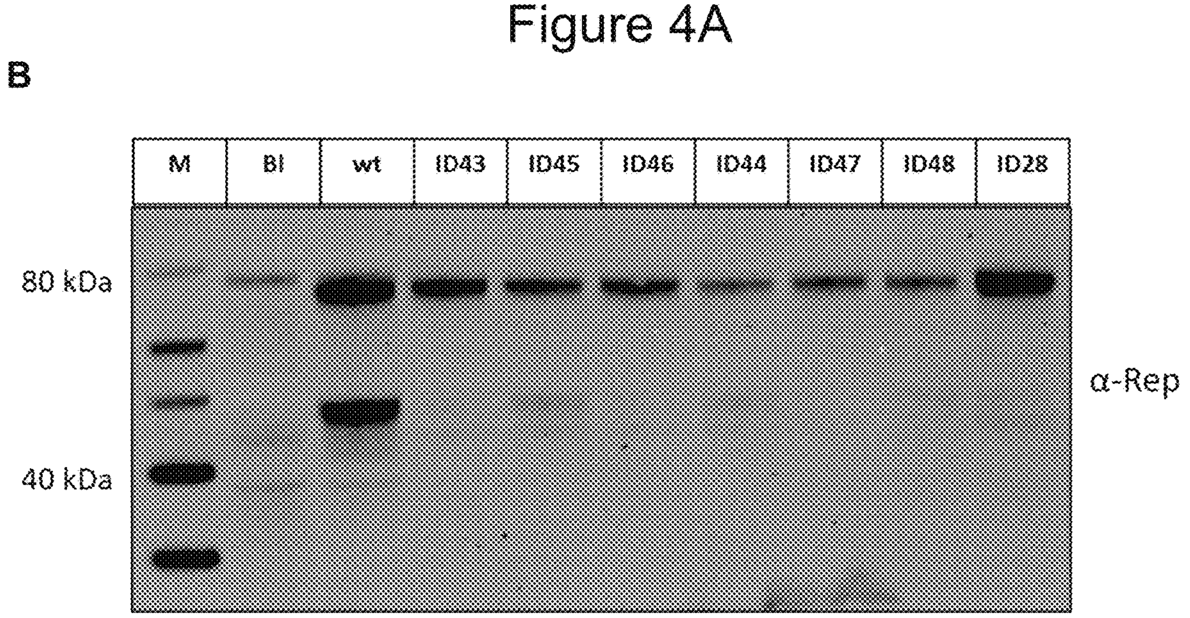
Figure 4C:
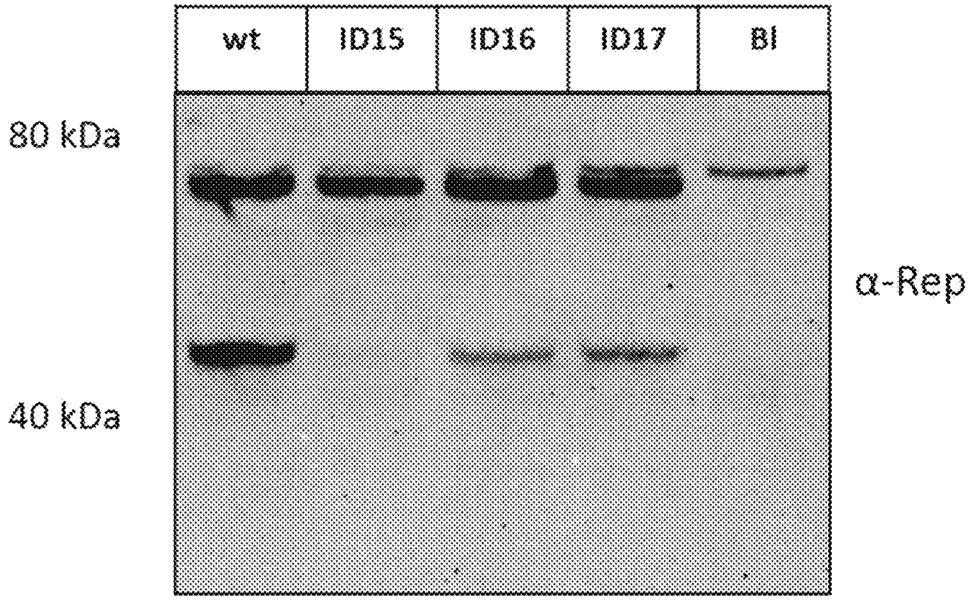
Figure 4D:
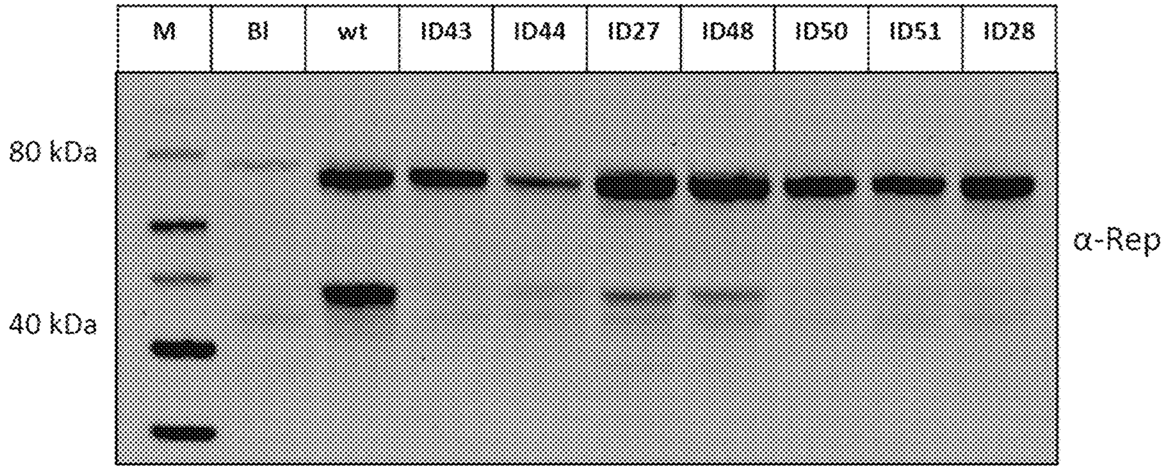
Figure 4E:
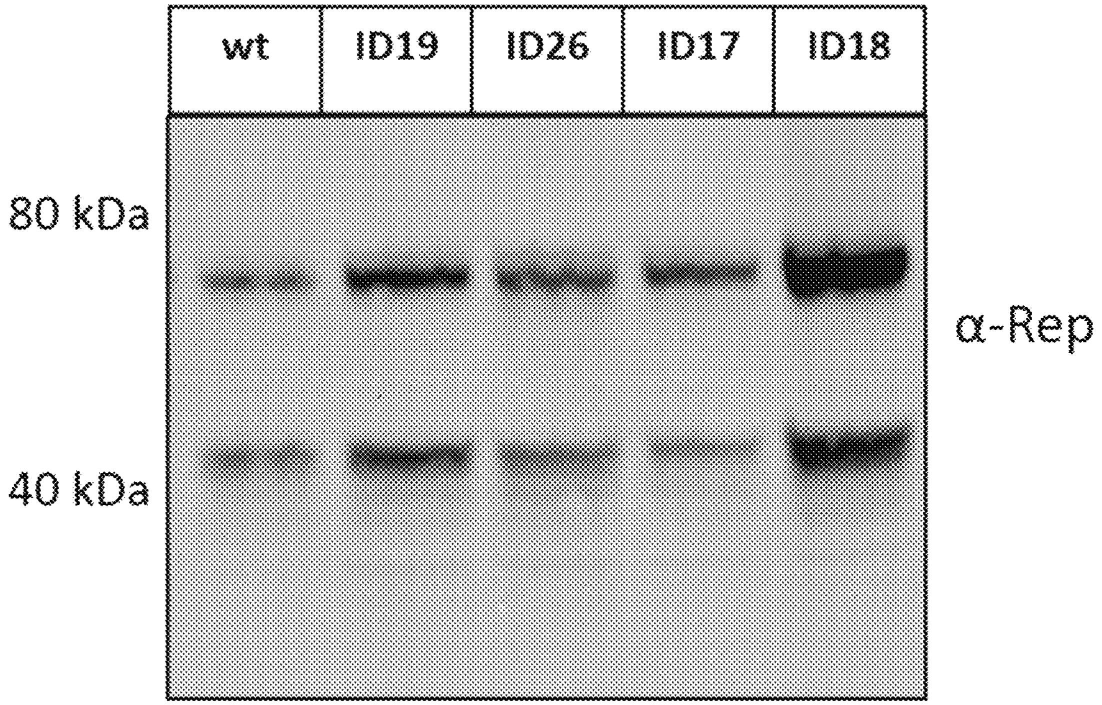
Figure 4F:
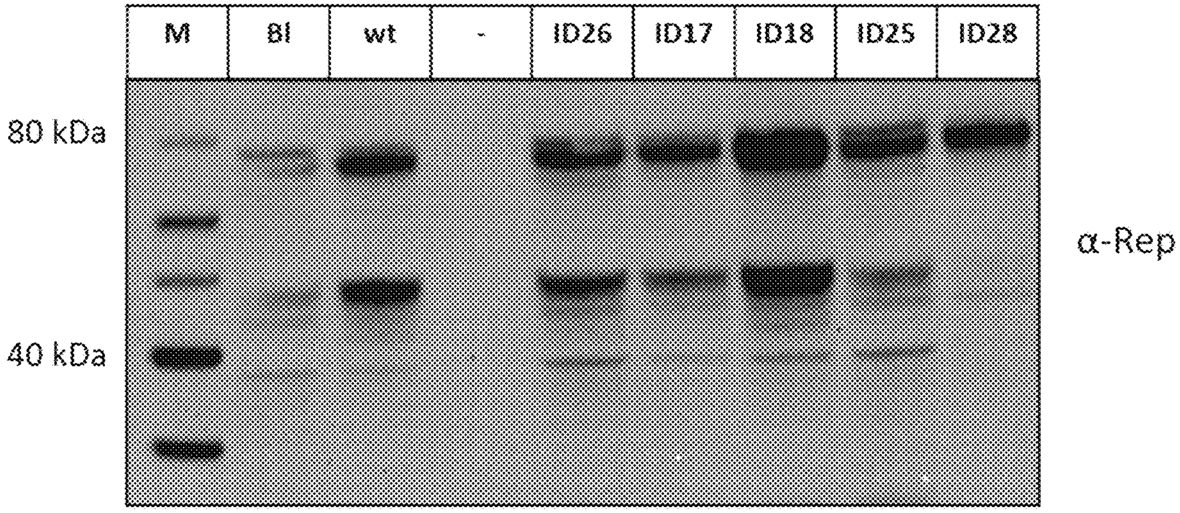
Figure 5A:
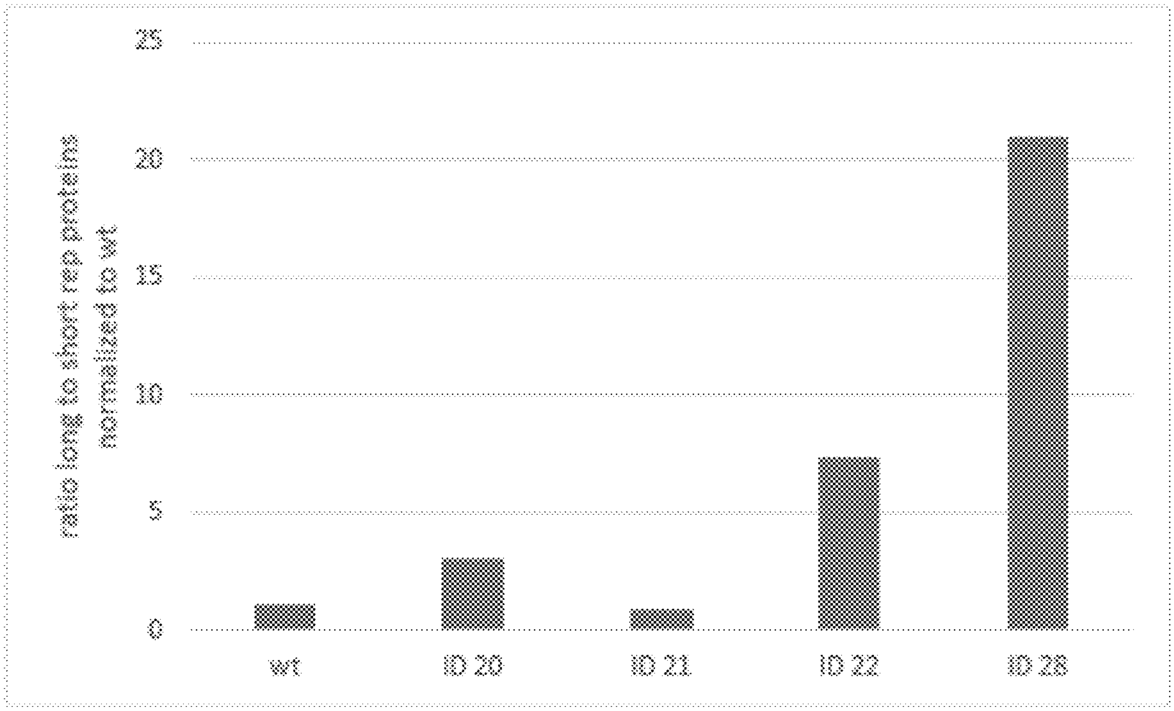
Figure 5B:
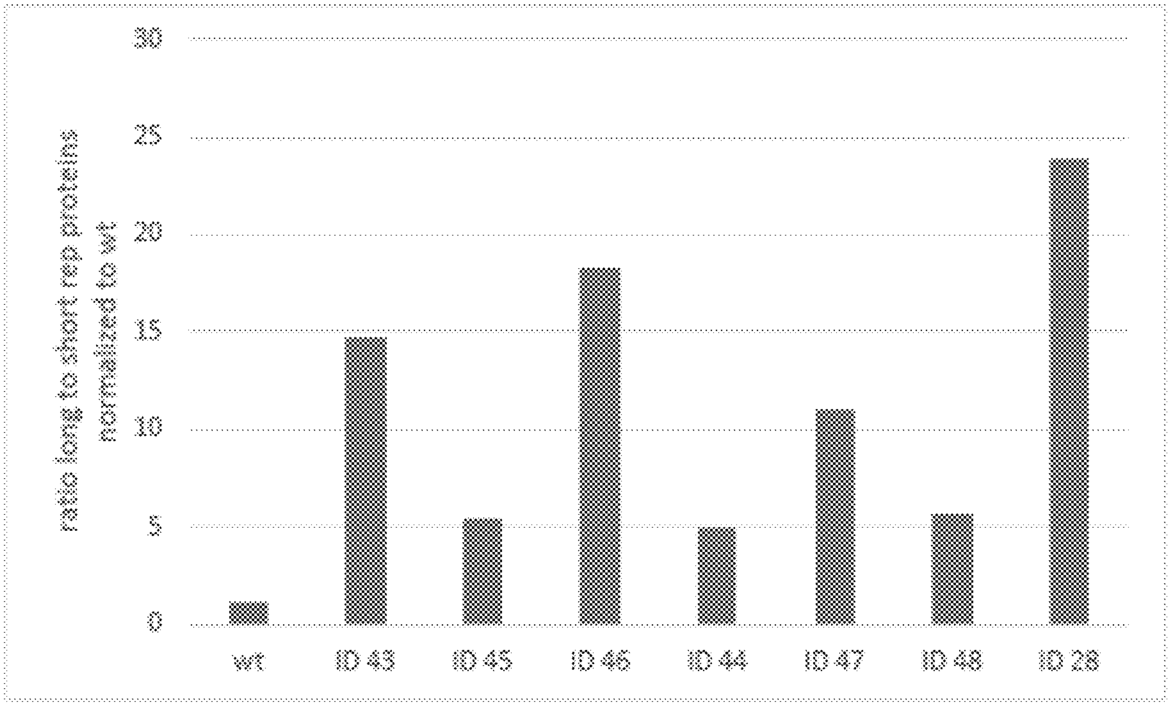
Figure 5C:
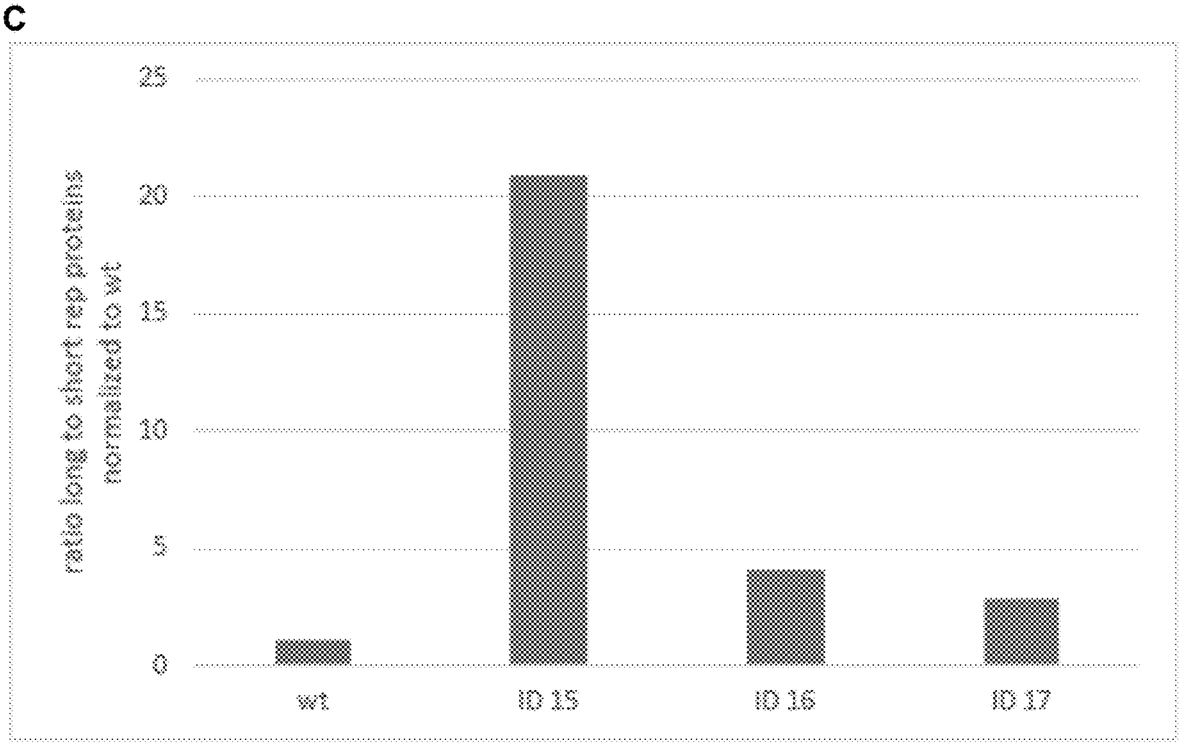
Figure 5D:
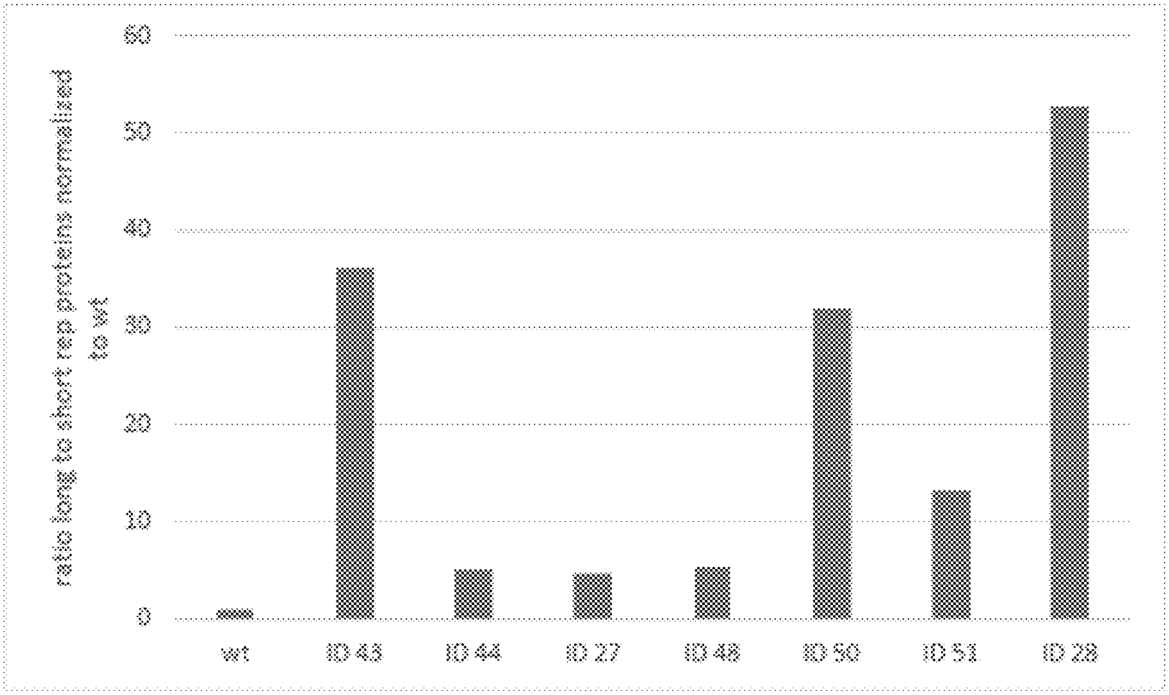
Figure 5E:
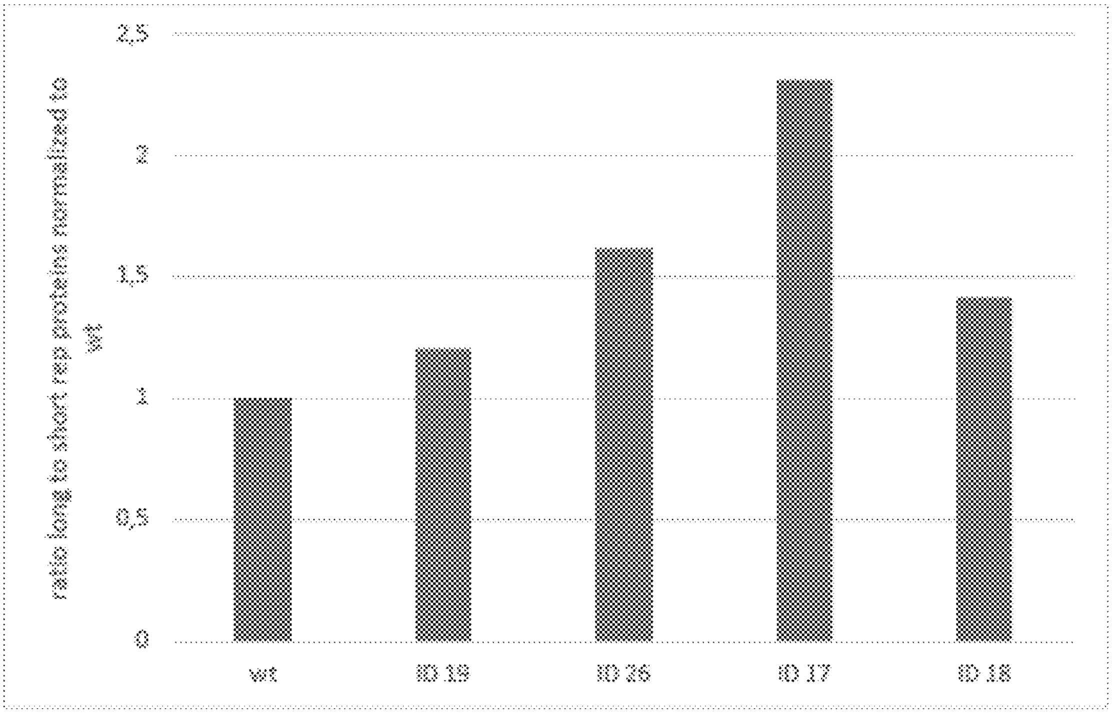
Figure 5F:
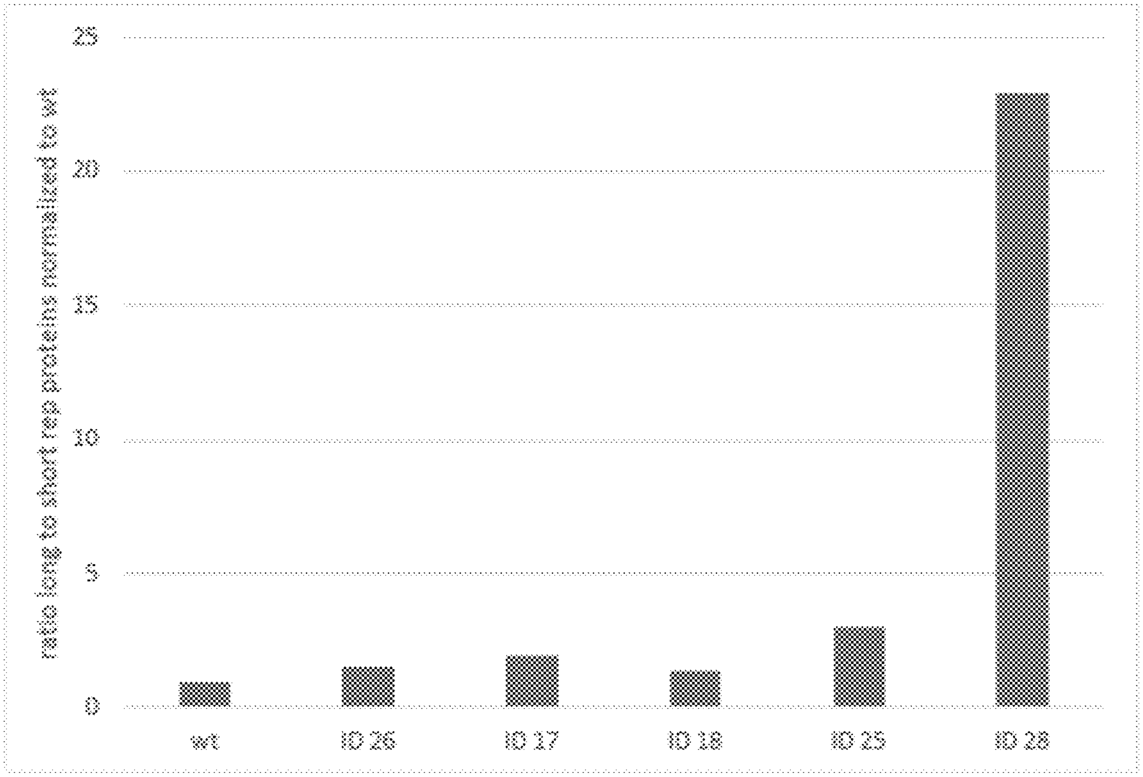

FIG. 3:

Overview of analyzed mutation patterns with SEQ ID NOs. of the corresponding AAV2 Rep proteins coding region (cf. also Table 2). The indication "SEQ-ID" in FIG. 3 refers to the respective SEQ ID NOs.

FIG. 4:

Expression of different Rep proteins in CAP cells upon transfection with different constructs containing silent mutations within the regulatory sequences of the p19 promoter (Table 2) and the wildtype construct (wt). Protein levels were detected in cell lysates of transiently transfected CAP-T cells 72 h post transfection using anti-replicase antibody (Progen). As control, cell lysate of non-transfected cells was included (BI). The indication of "ID" numbers in FIG. 4 refers to the respective SEQ ID NOs.

FIG. 5:

Quantification of anti-Rep western blots. Rep protein bands were quantified by densitometric analysis using ImageJ. Ratio of long to short Rep protein bands was calculated and wt was set to 1. All other values were normalized to wt. The indication of "ID" numbers in FIG. 5 refers to the respective SEQ ID NOs.

FIG. 6:

Inducible expression of the Rep proteins in a stable CAP derived cell line upon induction with 1 μg/mL doxycycline. Rep proteins were detected by immunoblot with anti-Replicase antibody (Progen). As control, cell lysate of non-induced cells was loaded (−Dox). At ~80 kDa, an unspecific background band is detected.

FIG. 7:

Induction of Rep proteins by addition of 1 μg/mL doxycycline in single cell clones derived from the stable cell line. Cells were transiently transfected with necessary components for rAAV5 production and induced with 1 μg/mL doxycycline 5 h after transfection. 72 h post transfection, cell lysates were prepared and expression of Rep proteins was detected by immunoblot with anti-Replicase antibody (Progen). The clones 5B6 and 2E3 do express very low levels of the long Rep proteins.

FIG. 8:

Viral titers of rAAV5 production by inducible Rep expressing clones. Viral genomes/mL were measured by qPCR with a primer/probe combination detecting the CMV-promoter using linearized transfer plasmid as standard. The single cell clones 5B6 and 2E3 do not show clear expression of long and short Rep proteins and therefore, do also only produce very low titers of rAAV5.

FIG. 9:

(A & B): Expression of different Rep proteins in CAP cells upon transfection with different constructs containing mutations within the regulatory sequences of the p19 promoter (Table 3) resulting in conservative amino acid exchanges and the wildtype construct (wt). Protein levels were detected in cell lysates of transiently transfected CAP-T cells 72 h post transfection using anti-replicase antibody (Progen). As control, cell lysate of non-transfected cells was included (BI).

(C): Viral production upon transfection of CAP cells with the following construct combination: pStbl-Rep-p19mut-ID 47, 48 or 37 or wt, pStbl-TRE3G-Rep50/42, pCMV-Tet3G, pHelper, pStbl-CMV-Cap5, pAAV-GFP. Viral genomes/mL were measured by qPCR with a primer/probe combination detecting the SV40 PolyA using linearized transfer plasmid as standard.

Figure 9A:
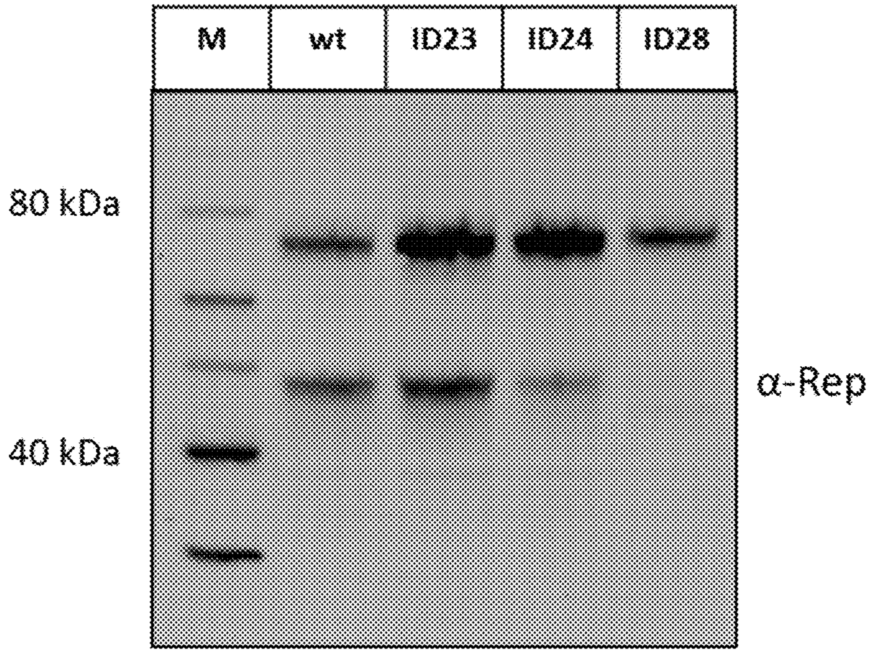
Figure 9B:
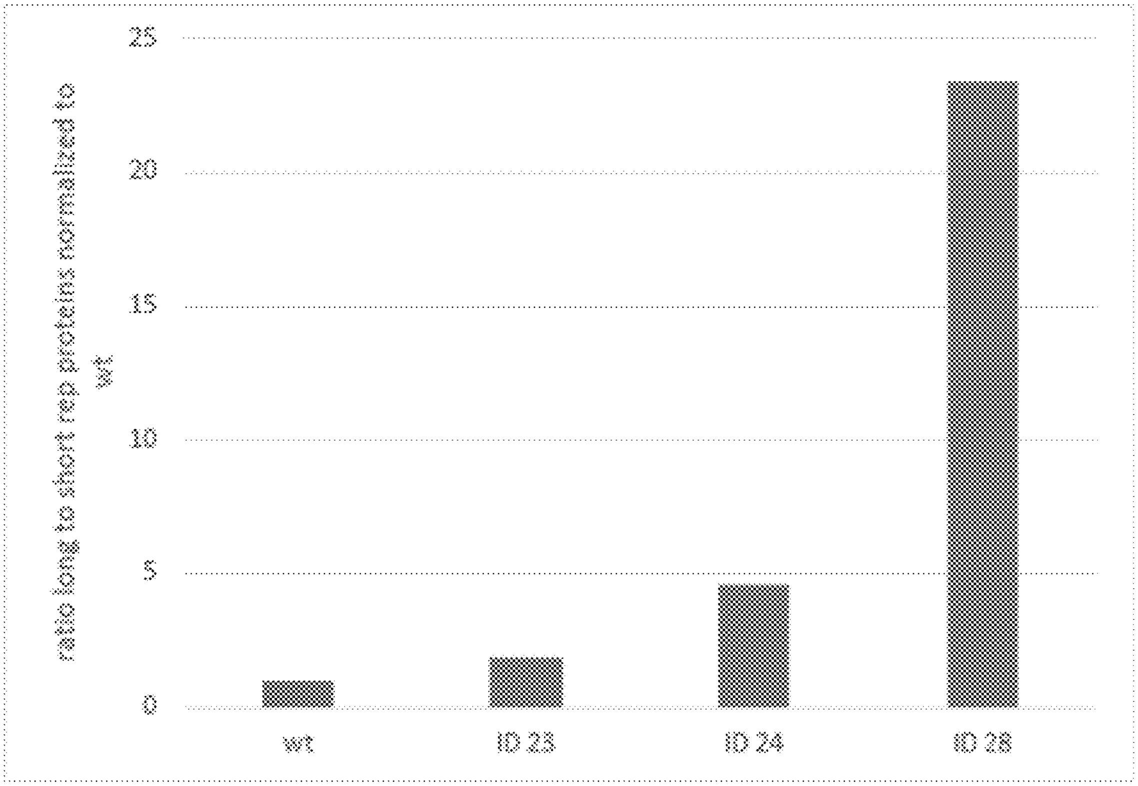

The indication of "ID" numbers in FIG. 9 refers to the respective SEQ ID NOs.

The present invention will be further illustrated in the following examples without being limited thereto.

EXAMPLES

Experimental Procedures

Cloning of Expression Constructs.

Synthesis of the rep locus of AAV2 with HpaI restriction sites at each end and regulatory sites within the p19 promoter. The genomic sequence of AAV2 was derived from GenBank: AF043303 (nucleotides 162 to 2332). The sequence of the synthetic locus is shown in SEQ ID NO: 29.

Different constructs for the p19 promoter region (nucleotides 651 to 1053 of the AAV2 genome) were designed containing different numbers of silent mutations within the regulatory sequences (Table 2) and produced synthetically.

Respective expression constructs were produced by standard cloning techniques and verified by sequencing. Components of the final expression constructs pStbl-bsd-Rep, pStbl-bsd-Rep-p19mut-SEQ ID NO: 1-14, 34-42 were the p5 promoter, the Rep locus containing either mutated or wt p19 promoter, a SV40 poly(A), a blasticidin selection cassette under the control of human Ubc promoter, an enhancing element for stable transcription of integrated ORFs, a pUC ori for propagation in *E. coli*, and an ampicillin resistance cassette for selection in *E. coli*.

A construct placing the Rep proteins under the control of a Tet-inducible promoter of the third generation (TRE3G-promoter) (FIG. 2) was produced by standard cloning techniques and verified by sequencing. The final sequence of this construct pStbl-bsd-TRE3G-Rep52/40-IRES-Rep78/68, starting from the TRE3G promoter until the SV40 poly(A) is shown in SEQ ID NO: 30. Components of pStbl-bsd-TRE3G-Rep52/40-IRES-Rep78/68 are the TRE3G promoter, the Rep locus starting from start codon of short Rep proteins, an IRES sequence of ECMV, the Rep locus containing mutated p19 promoter starting from start codon of long Rep proteins, a SV40 poly(A), a blasticidin selection cassette under the control of human Ubc promoter, and an enhancing element for stable transcription of integrated ORFs.

Cell Culture.

CAP cells were routinely cultivated in chemically defined, serum-free PEM medium (Thermo Fisher Scientific) supplemented with 4 mM L-alanyl-L-glutamine (Biochrom, Germany) in shake flasks (125 mL; Corning) on a shaking incubator at 185 rpm (5 cm orbit), 5% $CO_2$ and 37° C.

During routine cultivation, cells were diluted with fresh medium to a viable cell density of $1\times10^6$ cells/ml every 72 to 96 h. Viable cell density and viability were determined by trypan blue exclusion using a CEDEX XS cell counter (Innovatis, Roche Applied Science). Stable cell line expressing the Tet-on-3G-activator was cultivated in presence of 25 μg/mL G418; upon nucleofection with the pStbl-bsd-TRE3G-Rep50/42-IRES-Rep78/68 5 μg/mL blasticidin were added.

Transient Transfection and Western Blot to Test for Rep Protein Expression.

Transient transfection was performed using PEImax (PolySciences) in FreeStyle 293 medium (Thermo Fisher Scientific). 5 h post transfection, cells were fed with complete PEM medium (Thermo Fisher Scientific). An overview of generated transient transfection pools is found in Table 4, below.

Western Blot analysis was performed with cell lysates from $1\times10^5$ transfected cells utilizing mouse-anti-Replicase antibody (Progen, Germany) and horseradish peroxidase labeled anti-mouse antibody (Cell Signaling). Proteins were detected using the Pierce ECL WB Substrate Kit via chemiluminescence detector (INTAS).

Nucleofection and Generation of Stable Pools.

Stable pools were generated using Lonza's Nucleofector according to the manufacturer's instructions. A stable CAP cell line expressing the Tet-on-3G transactivator of the third generation was used for nucleofection with the inducible Rep-expression construct. For each nucleofection reaction, $1\times10^7$ cells were harvested by centrifugation (150×g, 5 min). The cells were resuspended in 100 μL complete nucleofector solution V (Lonza) and mixed with 5 μg of the linearized expression vector. The DNA/cell suspension was transferred into a cuvette and the nucleofection was performed using the X001 program. The transfected cells were transferred into 12.5 mL growth medium and cultured as described before at 37° C., 5% $CO_2$ at 185 rpm. For generation of stable pools, cells were pelleted by centrifugation and resuspended in selection medium (see Table 4) 72 to 96 h post-transfection following cultivation in a shaking incubator as described before.

TABLE 4

Generated CAP-T transient expression and CAP stable pools with corresponding expression vectors and media.

| Cell line | Plasmid | Selection medium |
|---|---|---|
| CAP-T | pStbl-bsd-Rep wt | transient |
| CAP-T | pStbl-bsd-Rep p19mut-ID 15 | transient |
| CAP-T | pStbl-bsd-Rep p19mut-ID 16 | transient |
| CAP-T | pStbl-bsd-Rep p19mut-ID 17 | transient |
| CAP-T | pStbl-bsd-Rep p19mut-ID 18 | transient |
| CAP-T | pStbl-bsd-Rep p19mut-ID 19 | transient |
| CAP-T | pStbl-bsd-Rep p19mut ID 20 | transient |
| CAP-T | pStbl-bsd-Rep p19mut-ID 21 | transient |
| CAP-T | pStbl-bsd-Rep p19mut-ID 22 | transient |
| CAP-T | pStbl-bsd-Rep p19mut-ID 25 | transient |
| CAP-T | pStbl-bsd-Rep p19mut-ID 26 | transient |
| CAP-T | pStbl-bsd-Rep p19mut-ID 27 | transient |
| CAP-T | pStbl-bsd-Rep p19mut-ID 28 | transient |
| CAP-T | pStbl-bsd-Rep p19mut-ID 43 | transient |
| CAP-T | pStbl-bsd-Rep p19mut-ID 44 | transient |
| CAP-T | pStbl-bsd-Rep p19mut-ID 45 | transient |
| CAP-T | pStbl-bsd-Rep p19mut-ID 46 | transient |
| CAP-T | pStbl-bsd-Rep p19mut-ID 47 | transient |
| CAP-T | pStbl-bsd-Rep p19mut-ID 48 | transient |
| CAP-T | pStbl-bsd-Rep p19mut-ID 49 | transient |
| CAP-T | pStbl-bsd-Rep p19mut-ID 50 | transient |
| CAP-T | pStbl-bsd-Rep p19mut-ID 51 | transient |
| CAP-T | pStbl-bsd-Rep p19mut-ID 23 | transient |
| CAP-T | pStbl-bsd-Rep p19mut-ID 24 | transient |
| CAP-Tet-on-3G | pStbl-bsd-TRE3G-Rep50/42-IRES-Rep78/68 | PEM + 4 mM Gln + 5 μg/mL blasticidin + 25 μg/mL G418 |

The indication of "ID" numbers in the above Table 4 refers to the respective SEQ ID NOs.

Induction and Transient Transfection to Test for AAV Production.

To test for AAV production by the stable single cell clones with inducible Rep expression, transient transfections were performed as described before. The following three constructs were used to provide the additional components for production of rAAV5 in a ratio of 1:1:0.5 (pAAV-GFP: pHelper:pStbl-CMV-Cap5). 5 h post transfection, a final concentration of 1 μg/mL doxycycline (Clontech) was added to induce expression of the Rep proteins.

72 h post transfection, cell suspension was harvested. Cells were lysed by addition of 0.5% Triton-X and incubation for 30 min at 37° C. with 1300 rpm. After centrifugation, supernatants were diluted 10-fold with buffer (50 mM Tris/HCl, pH 8.0; 2 mM $MgCl_2$) and incubated with 125 U/mL benzonase (Merck Millipore) for 2 h at 37° C. Addition of 2 mM EDTA and incubation at 70° C. for 10 min was used to inactivate the benzonase. Viral DNA was purified via the Pure Link Viral RNA/DNA mini kit (Thermo Fisher Scientific) according to the manufacturer's instructions.

qPCR to Determine Viral Titer.

The following primer/dual-labelled probe combination (ordered at MWG, Eurofins; Table 5) directed against the CMV promoter or the SV40 poly A were used to measure the viral titer:

TABLE 5

Primer/probe combination used for measuring the viral titer

| Primer/Probe | Sequence |
|---|---|
| CMV Primer for (SEQ ID NO: 31) | 5'-AAATGGCCCGCCTGGCATTATG-3' |
| CMV Primer rev (SEQ ID NO: 32) | 5'-AAACCGCTATCCACGCCCATTG-3' |

TABLE 5-continued

Primer/probe combination used for measuring the viral titer

| Primer/Probe | Sequence |
|---|---|
| CMV Probe (SEQ ID NO: 33) | ROX-5'-ACATGACCTTATGGGACTTTCCTACTTGGCAGTACATC-3'-BHQ2 |
| SV40 PolyA fw (SEQ ID NO: 52) | 5'-AGCAATAGCATCACAAATTTCACAA-3' |
| SV40 PolyA rev (SEQ ID NO: 53) | 5'-CCAGACATGATAAGATACATTGATGAGTT-3' |
| SV40 PolyA Probe (SEQ ID NO: 54) | FAM-5'-AGC ATT TTT TTC ACT GCA TTC TAG TTG TGG TTT GTC-3'-BHQ1 |

As standard, linearized transgene plasmid with a defined copy number was used. The qPCR reaction contained the following components: 2×Brilliant Multiplex qPCR Master Mix (Agilent), nuclease-free $H_2O$ (Thermo Fisher Scientific), primer/probe mix and sample/standard. qPCR was run on an Agilent Mx3005P according to the manufacturer's instructions.

Example 1

Effects of Silent Mutations on Expression of REP Proteins.

Introduction:

CAP cells are human amniocyte-derived suspension cells, which have been immortalized by stable transfection with a construct encoding E1A/E1B.

AAV Rep proteins are encoded by the AAV genome. There are in total four Rep proteins: Rep78 and Rep68 (expressed from p5 promoter); as well as Rep52 and Rep40 (expressed from p19 promoter located within coding region of long Rep proteins). These proteins mediate the replication and packaging of the AAV genome. However, said proteins are toxic for cells when stably expressed.

For the inactivation of the internal p19 promoter by introduction of silent mutations, regulatory elements of the p19 promoter were identified and different silent mutations not affecting the final protein sequence were inserted into the nucleotide sequence of these regulatory elements.

Results:

Expression of long and short Rep proteins was successfully separated by introducing silent mutations in the regulatory sequences of the p19 promoter. Most versions with mutations showed significantly reduced expression of the short Rep proteins. The reduction in expression of the short Rep proteins was already visible upon introducing one single mutation becoming more pronounced when introducing up to 20 mutations (FIG. 4, FIG. 5). Separating the 5' and 3' motifs showed that especially the 3' motifs next to the promoter (SP1 −50; TATA −35, TATA −20) are important for the activation of the internal p19 promoter. Mutating only the TATA −20 motif led to a significant but not full reduction of expression of the short rep proteins suggesting that also SP1 −50 and TATA −35 are important for the activation of expression, supported further by the fact that mutating everything except the TATA −20 also resulted in a clear decrease of expression of the short rep proteins. Looking closer at the single motifs, especially the SP1 −50 motif and more exactly the mutation 824G>H resulted in a very clear reduction of the expression of the short rep proteins. In addition, mutation of TATA −20 clearly reduced expression of short rep proteins. For TATA −35, only the combination of the different mutations within the motif resulted in a very clear decrease with the mutation 848A>G having the biggest effect on expression.

To generate a stable cell line inducibly expressing Rep proteins, the genes for the long Rep proteins carrying the silent mutations and the genes for the short Rep proteins were separated and each put under control of an inducible promoter. For the further experiments, the p19mut construct with the 19 mutations was chosen.

Example 2

Generation of Stable CAP Clones Inducibly Expressing Rep Proteins of AAV2.

Introduction:

For the generation of an inducible expression cassette for AAV2 Rep proteins the p19mut variant with 19 silent mutations was selected.

Figure 2:

Tet-inducible promoters of the third generation (TRE3G-promoter) were used to regulate expression of the Rep proteins by doxycycline addition (overview of construct see FIG. 2). CAP cells expressing the Tet-on-3G transactivator were previously generated by nucleofection and selection with 25 μg/mL G418. The pStbl-bsd-TRE3G-Rep52/40-IRES-Rep78/68 construct was nucleofected in this stable pool and selected with 5 μg/mL blasticidin. Single cell cloning using limiting dilutions was performed and clones were screened by western blot for Rep proteins.

Figure 6:
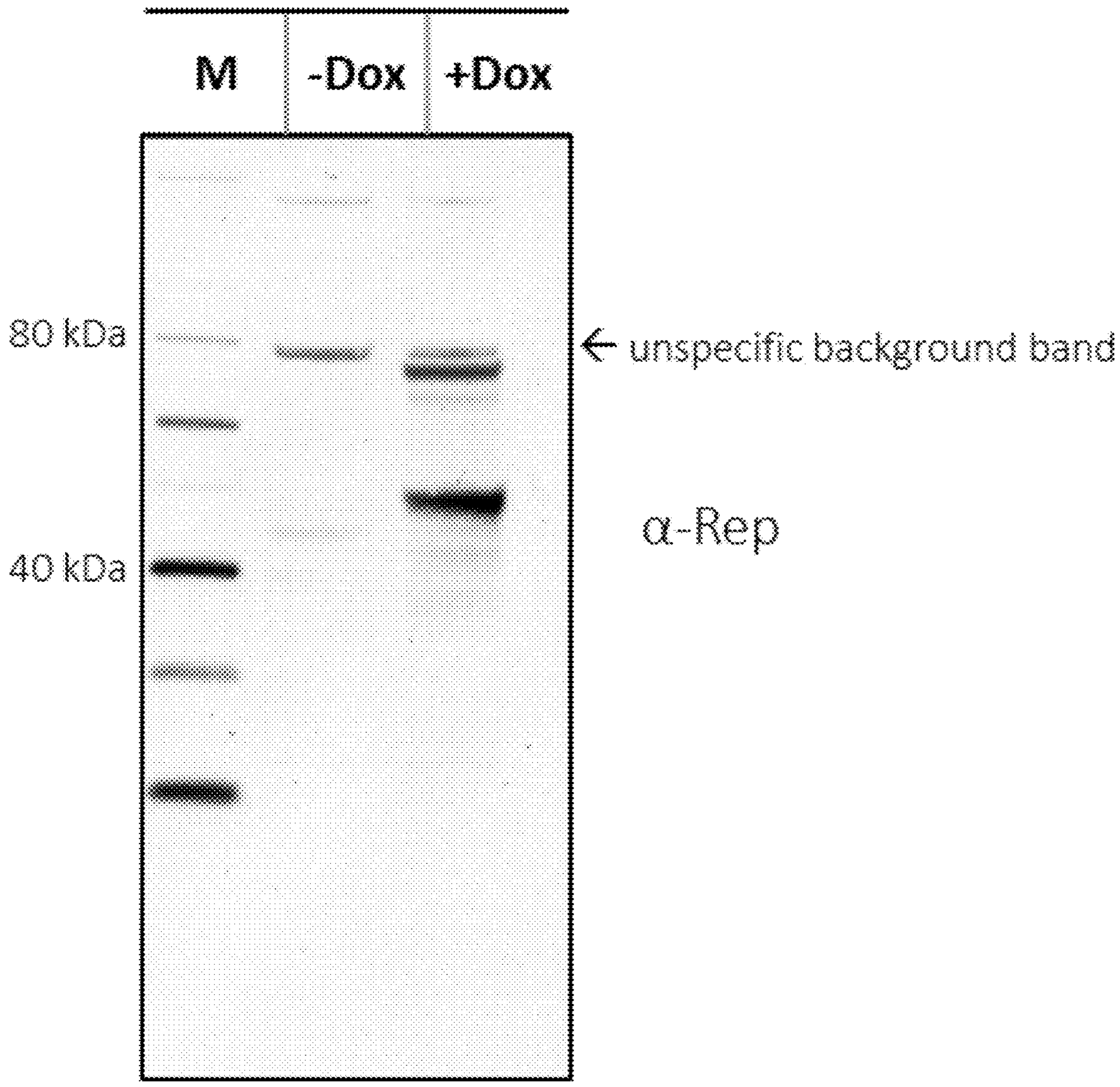

Results:

A stable CAP cell pool carrying the Tet-on-3G transactivator and the pStbl-bsd-TRE3G-Rep52/40-IRES-Rep78/68 was analyzed by Western blot for expression of the different rep protein before and after induction with doxycyclin (FIG. 6). Without Doxycyclin induction, no signals specific for the Rep proteins could be detected, whereas both long and short Rep proteins were expressed upon Doxycyclin induction.

Figure 7:
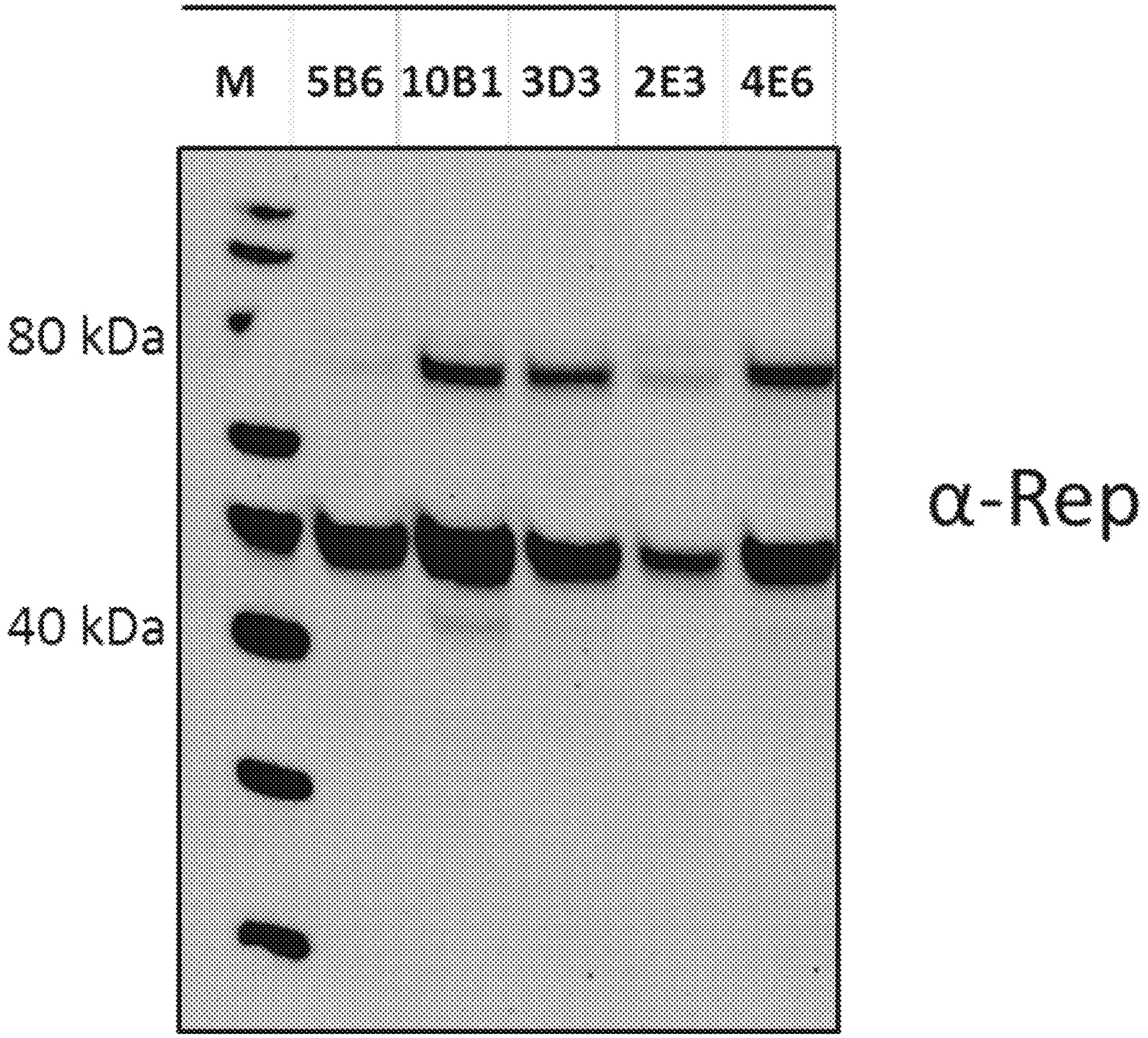

From the stable pool, single cell-derived clones were generated by limiting dilution. The single cell-derived clones were analyzed for expression of the Rep proteins after Doxycyclin induction. Out of 5 clones, 3 clones expressed both the long and the short Rep proteins in the expected ratio, whereas 2 of the clones displayed reduced levels of the long Rep proteins (FIG. 7).

The data shows that using rep constructs with silent mutations in the p19 promoter, clonal cell populations with inducible expression of both long and short Rep proteins can be generated. Such clones can serve as a basis for the generation of packaging/producer cell lines.

Example 3

Production of AAV in stable CAP clones inducibly expressing Rep proteins of AAV2.

Introduction:

To proof that the inducible Rep cell lines are capable of producing AAV vectors, the missing components for AAV production were transiently introduced into cells of the 5 different clones:

Capsid proteins from AAV5, cloned under control of CMV promoter in pStbl vector, the additional helper genes E2A, E4orf6, VA RNA, as well as the transfer vector with gene of interest (GOI): pAAV-GFP.

Figure 8:
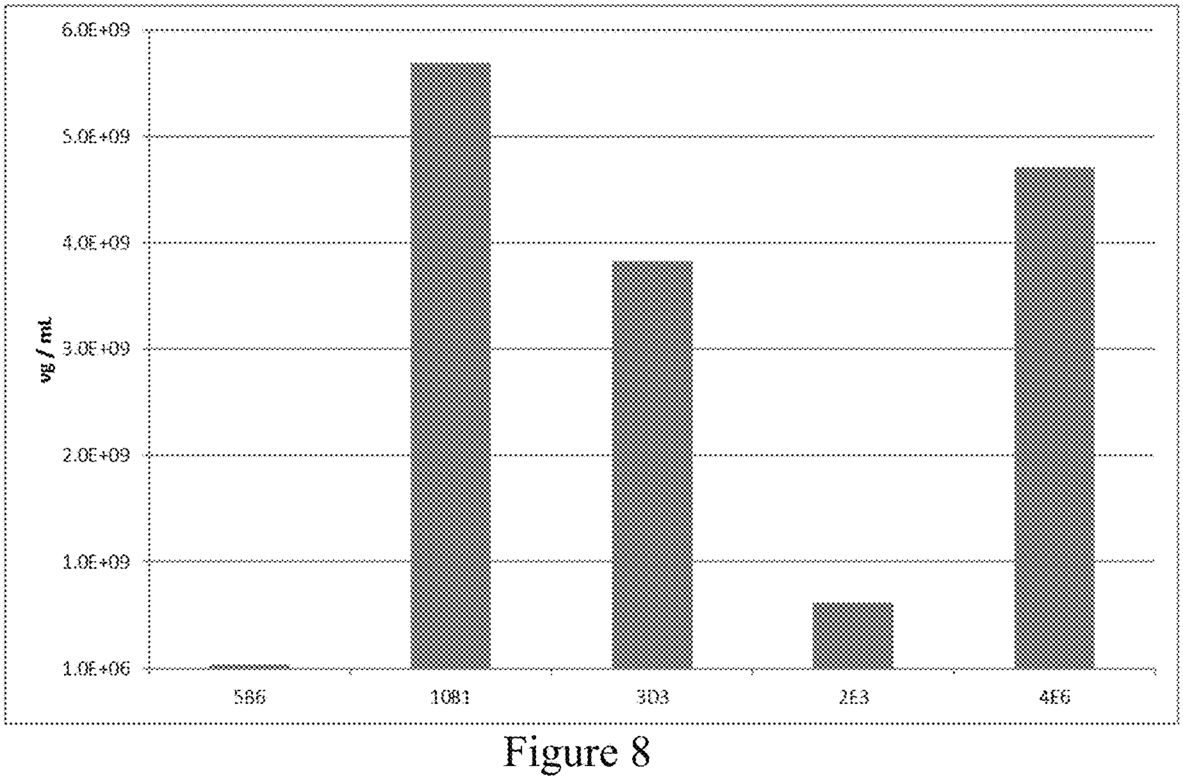

Results:

Using single cell clones of the stable Rep inducible expressing cell line, AAV production could be shown upon transfecting the cells with the lacking necessary components and doxycycline induction (FIG. 8). The two clones with lower levels of long Rep proteins also showed lower AAV titers as expected. This proofs that this approach results in production of viral vectors, and that the generation of a high producing AAV packaging cell line is now possible.

Example 4

AAV Production Using Rep Proteins with Conservative Amino Acid Exchange

For the inactivation of the internal p19 promoter by introduction of mutations in the promoter regions resulting in conservative amino acid exchanges, regulatory elements of the p19 promoter were identified. Three distinct mutations, 846T>G, 847T>C, 848A>B, were inserted into the nucleotide sequence of the TATA −20 region resulting in a conservative Leu176>Ala exchange (ID23). Two distinct mutations, 823C>G, 824G>H, were inserted into the nucleotide sequence of the SP1 −50 region resulting in a conservative Ala168>Gly exchange (ID24). The different constructs were transiently introduced into CAP-T cells and the expression level of the long and short Rep proteins was analyzed and compared to the wt and mut-20 (ID28) (FIG. 9 A, B).

To proof the functionality of the long rep proteins with conservative amino acid exchanges in the TATA −20 or the SP1 −50 region, AAV was produced by introducing the following construct combination transiently into the CAP-T cells: a construct coding for the long Rep proteins, either pStbl-Rep-p19mut-ID23, or -ID24, or -mut20, or -wt, together with the a construct encoding for the short Rep proteins (pStbl-TRE3G-Rep50/42), pCMV-Tet3G, and the additional helper genes E2A, E4orf6, VA RNA, as well as the transfer vector with gene of interest (GOI), pAAV-GFP (FIG. 9 C).

Results:

Western blot analysis revealed that the expression of long and short Rep proteins was successfully separated by introducing distinct mutations in the regulatory sequences of the p19 promoter resulting in conservative aa exchanges either in the SP1 −50 or in the TATA −20 region.

As before the mutation in the SP1 −50 region had a more pronounced effect that the introduced mutations in the TATA −20 box, confirming the important role of SP1 −50 (FIG. 9 A, B).

Figure 9C:
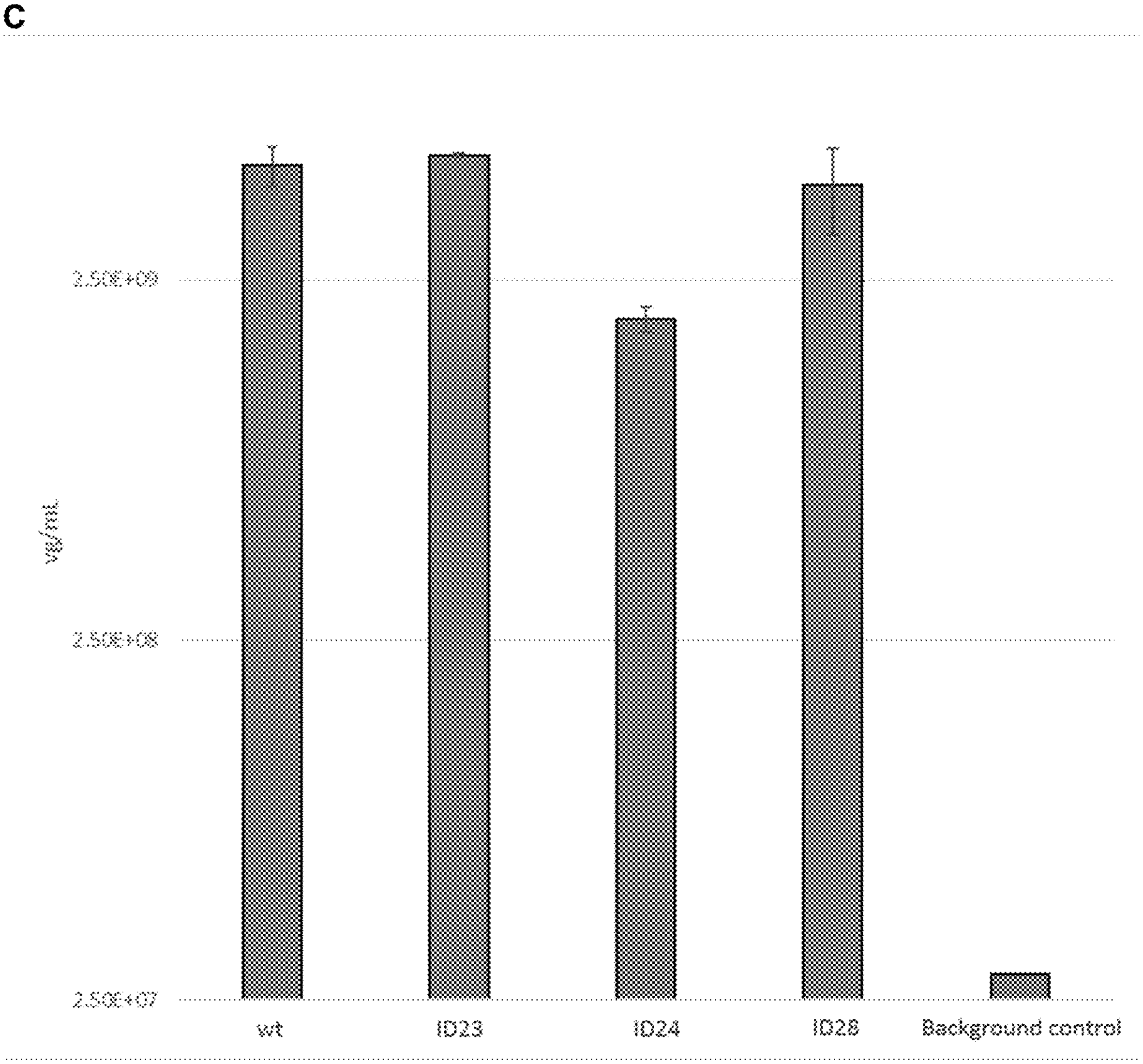

Importantly the functionality of the long Rep proteins harboring the Leu176>Ala (ID23) or Ala168>Gly (ID24) exchange could be proven by the production of AAV particle via transient production. The titer of the AAV particle produced with the Rep proteins harboring the conservative amino acid exchange are in the same range as the wt or the mut-20 control, with some reduction of the AAV titer in the ID24 sample (FIG. 9C).

The present invention relates to the following nucleotide sequences.

SEQ ID NO: 1
AAV2 mutated p19 promoter region mut19
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACDCGBAACGGCGCCGGGGGDGGHAACAAAGTHGTHGATGAGTGCTAC
ATCCCCAATTACTTGCTCCCCAAAACCCAGCCTGAGCTCCAATGGGCHTGGACVAACATGGAA
CAGTACTTGTCDGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 2
AAV2 mutated p19 promoter region mut5
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTACTTGTCDGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 3
AAV2 mutated p19 promoter region mut1
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTATTTGAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

```
SEQ ID NO: 4
AAV2 mutated p19 promoter region mut2
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTATTTATCCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 5
AAV2 mutated p19 promoter region mut1-2
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTACTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 6
AAV2 mutated p19 promoter region mut14
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACDCGBAACGGCGCCGGGGGDGGHAACAAAGTHGTHGATGAGTGCTAC
ATCCCCAATTACTTGCTCCCCAAAACCCAGCCTGAGCTCAATGGGCHTGGACVAACATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 7
AAV2 mutated p19 promoter region mut10
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACDCGBAACGGCGCCGGGGGDGGHAACAAAGTHGTHGATGAGTGCTAC
ATCCCCAATTACTTGCTCCCCAAAACCCAGCCTGAGCTCCAGTGGGCGTGGACTAATATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 8
AAV2 mutated p19 promoter region mut10-2
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCAATGGGCHTGGACVAACATGGAA
CAGTACCTBTCDGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 9
AAV2 mutated p19 promoter region mut3
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTATGCBAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 10
AAV2 mutated p19 promoter region mut2-2
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGGHTGGACTAATATGGAA
```

-continued

CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG

SEQ ID NO: 11
AAV2 mutated p19 promoter region mut2-3
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTATCTBAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 12
AAV2 mutated p19 promoter region mut1-3
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTATCTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 13
AAV2 mutated p19 promoter region mut5-2
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAATATGGAA
CAGTACCTBTCCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 14
AAV2 mutated p19 promoter region mut20
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACDCGBAACGGCGCCGGGGGDGGHAACAAAGTHGTHGATGAGTGCTAC
ATCCCCAATTACTTGCTCCCCAAAACCCAGCCTGAGCTCCAATGGGCHTGGACVAACATGGAA
CAGTACCTBTCDGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 15
AAV2 Rep proteins coding region with mutated p19 promoter region mut19
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACDCGBAACGGCGCCGGGGGDGGHAACAAAGTH
GTHGATGAGTGCTACATCCCCAATTACTTGCTCCCCAAAACCCAGCCTGAGCTCCAATGGGCH
TGGACVAACATGGAACAGTACTTGTCDGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC -continued AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 16
AAV2 Rep proteins coding region with mutated p19 promoter region mut5
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTACTTGTCDGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 17
AAV2 Rep proteins coding region with mutated p19 promoter region mut1
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTATTTGAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC -continued TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 18
AAV2 Rep proteins coding region with mutated p19 promoter region mut2
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTATTTATCCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 19
AAV2 Rep proteins coding region with mutated p19 promoter region mut1-2
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTACTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA -continued SEQ ID NO: 20
AAV2 Rep proteins coding region with mutated p19 promoter region mut14
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACDCGBAACGGCGCCGGGGGDGGHAACAAAGTH
GTHGATGAGTGCTACATCCCCAATTACTTGCTCCCCAAAACCCAGCCTGAGCTCCAATGGGCH
TGGACVAACATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 21
AAV2 Rep proteins coding region with mutated p19 promoter region mut10
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACDCGBAACGGCGCCGGGGGDGGHAACAAAGTH
GTHGATGAGTGCTACATCCCCAATTACTTGCTCCCCAAAACCCAGCCTGAGCTCCAGTGGGCG
TGGACTAATATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 22
AAV2 Rep proteins coding region with mutated p19 promoter region mut10-2
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT -continued CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAATGGGCH
TGGACVAACATGGAACAGTACCTBTCDGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 23
AAV2 Rep proteins coding region with mutated p19 promoter region mut3
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTATGCBAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 24
AAV2 Rep proteins coding region with mutated p19 promoter region mut2-2
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGGH
TGGACTAATATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT -continued TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 25
AAV2 Rep proteins coding region with mutated p19 promoter region mut2-3
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTATCTBAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 26
AAV2 Rep proteins coding region with mutated p19 promoter region mut1-3
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTATCTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA -continued AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 27
AAV2 Rep proteins coding region with mutated p19 promoter region mut5-2
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAATATGGAACAGTACCTBTCCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 28
AAV2 Rep proteins coding region with mutated p19 promoter region mut20
bold: regulatory sites within the p19 promoter
underlined: mutation in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACDCGBAACGGCGCCGGGGGDGGHAACAAAGTH
GTHGATGAGTGCTACATCCCCAATTACTTGCTCCCCAAAACCCAGCCTGAGCTCCAATGGGCH
TGGACVAACATGGAACAGTACCTBTCDGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG -continued CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 29
Synthetic AAV2 rep locus
bold: regulatory sites within the p19 promoter
underlined: HpaI restriction sites
GTTAACTGACGTGAATTACGTCATAGGGTTAGGGAGGTCCTGTATTAGAGGTCACGTGAGTGT
TTTGCGACATTTTGCGACACCATGTGGTCACGCTGGGTATTTAAGCCCGAGTGAGCACGCAGG
GTCTCCATTTTGAAGCGGGAGGTTTGAACGCGCAGCCGCCATGCCGGGGTTTTACGAGATTGT
GATTAAGGTCCCCAGCGACCTTGACGAGCATCTGCCCGGCATTTCTGACAGCTTTGTGAACTG
GGTGGCCGAGAAGGAATGGGAGTTGCCGCCAGATTCTGACATGGATCTGAATCTGATTGAGCA
GGCACCCCTGACCGTGGCCGAGAAGCTGCAGCGCGACTTTCTGACGGAATGGCGCCGTGTGAG
TAAGGCCCCGGAGGCCCTTTTCTTTGTGCAATTTGAGAAGGGAGAGAGCTACTTCCACATGCA
CGTGCTCGTGGAAACCACCGGGGTGAAATCCATGGTTTTGGGACGTTTCCTGAGTCAGATTCG
CGAAAAACTGATTCAGAGAATTTACCGCGGGATCGAGCCGACTTTGCCAAACTGGTTCGCGGT
CACAAAGACCAGAAATGGCGCCGGAGGCGGGAACAAGGTGGTGGATGAGTGCTACATCCCCAA
TTACTTGCTCCCCAAAACCCAGCCTGAGCTCCAGTGGGCGTGGACTAATATGGAACAGTATTT
AAGCGCCTGTTTGAATCTCACGGAGCGTAAACGGTTGGTGGCGCAGCATCTGACGCACGTGTC
GCAGACGCAGGAGCAGAACAAAGAGAATCAGAATCCCAATTCTGATGCGCCGGTGATCAGATC
AAAAACTTCAGCCAGGTACATGGAGCTGGTCGGGTGGCTCGTGGACAAGGGGATTACCTCGGA
GAAGCAGTGGATCCAGGAGGACCAGGCCTCATACATCTCCTTCAATGCGGCCTCCAACTCGCG
GTCCCAAATCAAGGCTGCCTTGGACAATGCGGGAAAGATTATGAGCCTGACTAAAACCGCCCC
CGACTACCTGGTGGGCCAGCAGCCCGTGGAGGACATTTCCAGCAATCGGATTTATAAAATTTT
GGAACTAAACGGGTACGATCCCCAATATGCGGCTTCCGTCTTTCTGGGATGGGCCACGAAAAA
GTTCGGCAAGAGGAACACCATCTGGCTGTTTGGGCCTGCAACTACCGGGAAGACCAACATCGC
GGAGGCCATAGCCCACACTGTGCCCTTCTACGGGTGCGTAAACTGGACCAATGAGAACTTTCC
CTTCAACGACTGTGTCGACAAGATGGTGATCTGGTGGGAGGAGGGGAAGATGACCGCCAAGGT
CGTGGAGTCGGCCAAAGCCATTCTCGGAGGAAGCAAGGTGCGCGTGGACCAGAAATGCAAGTC
CTCGGCCCAGATAGACCCGACTCCCGTGATCGTCACCTCCAACACCAACATGTGCGCCGTGAT
TGACGGGAACTCAACGACCTTCGAACACCAGCAGCCGTTGCAAGACCGGATGTTCAAATTTGA
ACTCACCCGCCGTCTGGATCATGACTTTGGGAAGGTCACCAAGCAGGAAGTCAAAGACTTTTT
CCGGTGGGCAAAGGATCACGTGGTTGAGGTGGAGCATGAATTCTACGTCAAAAAGGGTGGAGC
CAAGAAAAGACCCGCCCCCAGTGACGCAGATATAAGTGAGCCCAAACGGGTGCGCGAGTCAGT
TGCGCAGCCATCGACGTCAGACGCGGAAGCTTCGATCAACTACGCAGACAGGTACCAAAACAA
ATGTTCTCGTCACGTGGGCATGAATCTGATGCTGTTTCCCTGCAGACAATGCGAGAGAATGAA
TCAGAATTCAAATATCTGCTTCACTCACGGACAGAAAGACTGTTTAGAGTGCTTTCCCGTGTC
AGAATCTCAACCCGTTTCTGTCGTCAAAAAGGCGTATCAGAAACTGTGCTACATTCATCATAT
CATGGGAAAGGTGCCAGACGCTTGCACTGCCTGCGATCTGGTCAATGTGGATTTGGATGACTG
CATCTTTGAACAATAAATGATTTAAATCAGGTATGGCTGCCGATGGTTATCTTCCAGATTGGC
TCGAGGACACTCTCTCTGAAGGAATAAGACAGTGGTGGAAGCTCAAACCTGGCCCACCACCAC
CAAAGCCCGCAGAGCGGCATAAGGACGACAGCAGGGGTTAAC SEQ ID NO: 30
Inducible expression construct for AAV2 Rep proteins
GTTTACTCCCTATCAGTGATAGAGAACGTATGAAGAGTTTACTCCCTATCAGTGATAGAGAAC
GTATGCAGACTTTACTCCCTATCAGTGATAGAGAACGTATAAGGAGTTTACTCCCTATCAGTG
ATAGAGAACGTATGACCAGTTTACTCCCTATCAGTGATAGAGAACGTATCTACAGTTTACTCC
CTATCAGTGATAGAGAACGTATATCCAGTTTACTCCCTATCAGTGATAGAGAACGTATAAGCT
TTAGGCGTGTACGGTGGGCGCCTATAAAAGCAGAGCTCGTTTAGTGAACCGTCAGATCGCCTG
GAGCAATTCCACAACACTTTTGTCTTATACCAACTTTCCGTACCACTTCCTACCCTCGTAAAG
TCGACACCGGGGCCCAGATCTATCGATCGGCCGGATAACGCCACCATGGAGCTGGTCGGGTGG
CTCGTGGACAAGGGGATTACCTCGGAGAAGCAGTGGATCCAGGAGGACCAGGCCTCATACATC
TCCTTCAATGCGGCCTCCAACTCGCGGTCCCAAATCAAGGCTGCCTTGGACAATGCGGGAAAG
ATTATGAGCCTGACTAAAACCGCCCCCGACTACCTGGTGGGCCAGCAGCCCGTGGAGGACATT
TCCAGCAATCGGATTTATAAAATTTTGGAACTAAACGGGTACGATCCCCAATATGCGGCTTCC
GTCTTTCTGGGATGGGCCACGAAAAAGTTCGGCAAGAGGAACACCATCTGGCTGTTTGGGCCT
GCAACTACCGGGAAGACCAACATCGCGGAGGCCATAGCCCACACTGTGCCCTTCTACGGGTGC
GTAAACTGGACCAATGAGAACTTTCCCTTCAACGACTGTGTCGACAAGATGGTGATCTGGTGG
GAGGAGGGGAAGATGACCGCCAAGGTCGTGGAGTCGGCCAAAGCCATTCTCGGAGGAAGCAAG
GTGCGCGTGGACCAGAAATGCAAGTCCTCGGCCCAGATAGACCCGACTCCCGTGATCGTCACC
TCCAACACCAACATGTGCGCCGTGATTGACGGGAACTCAACGACCTTCGAACACCAGCAGCCG
TTGCAAGACCGGATGTTCAAATTTGAACTCACCCGCCGTCTGGATCATGACTTTGGGAAGGTC
ACCAAGCAGGAAGTCAAAGACTTTTTCCGGTGGGCAAAGGATCACGTGGTTGAGGTGGAGCAT
GAATTCTACGTCAAAAAGGGTGGAGCCAAGAAAAGACCCGCCCCCAGTGACGCAGATATAAGT
GAGCCCAAACGGGTGCGCGAGTCAGTTGCGCAGCCATCGACGTCAGACGCGGAAGCTTCGATC
AACTACGCAGACAGGTACCAAAACAAATGTTCTCGTCACGTGGGCATGAATCTGATGCTGTTT
CCCTGCAGACAATGCGAGAGAATGAATCAGAATTCAAATATCTGCTTCACTCACGGACAGAAA
GACTGTTTAGAGTGCTTTCCCGTGTCAGAATCTCAACCCGTTTCTGTCGTCAAAAAGGCGTAT
CAGAAACTGTGCTACATTCATCATATCATGGGAAAGGTGCCAGACGCTTGCACTGCCTGCGAT
CTGGTCAATGTGGATTTGGATGACTGCATCTTTGAACAATAAATGATTTAAATCAGGTATGGC
TGCCGATGGTTATCTTCCAGATTGGCTCGAGGACACTCTCTCTGAGATAACTGAGGGATAGAA
TTCCGCCCCCCCCCCCTAACGTTACTGGCCGAAGCCGCTTGGAATAAGGCCGGTGTGCGTTTG
TCTATATGTTATTTTCCACCATATTGCCGTCTTTTGGCAATGTGAGGGCCCGGAAACCTGGCC -continued CTGTCTTCTTGACGAGCATTCCTAGGGGTCTTTCCCCTCTCGCCAAAGGAATGCAAGGTCTGT
TGAATGTCGTGAAGGAAGCAGTTCCTCTGGAAGCTTCTTGAAGACAAACAACGTCTGTAGCGA
CCCTTTGCAGGCAGCGGAACCCCCCACCTGGCGACAGGTGCCTCTGCGGCCAAAAGCCACGTG
TATAAGATACACCTGCAAAGGCGGCACAACCCCAGTGCCACGTTGTGAGTTGGATAGTTGTGG
AAAGAGTCAAATGGCTCTCCTCAAGCGTATTCAACAAGGGGCTGAAGGATGCCCAGAAGGTAC
CCCATTGTATGGGATCTGATCTGGGGCCTCGGTGCACATGCTTTACATGTGTTTAGTCGAGGT
TAAAAAAACGTCTAGGCCCCCCGAACCACGGGGACGTGGTTTTC+32TGAAAAACACGATGAT
AATAGTTATCGCCGCCATGCCGGGGTTTTACGAGATTGTGATTAAGGTCCCCAGCGACCTTGA
CGAGCATCTGCCCGGCATTTCTGACAGCTTTGTGAACTGGGTGGCCGAGAAGGAATGGGAGTT
GCCGCCAGATTCTGACATGGATCTGAATCTGATTGAGCAGGCACCCCTGACCGTGGCCGAGAA
GCTGCAGCGCGACTTTCTGACGGAATGGCGCCGTGTGAGTAAGGCCCCGGAGGCCCTTTTCTT
TGTGCAATTTGAGAAGGGAGAGAGCTACTTCCACATGCACGTGCTCGTGGAAACCACCGGGGT
GAAATCCATGGTTTTGGGACGTTTCCTGAGTCAGATTCGCGAAAAACTGATTCAGAGAATTTA
CCGCGGGATCGAGCCGACTTTGCCAAACTGGTTCGCGGTCACAAAGACACGGAACGGCGCCGG
GGGAGGCAACAAAGTCGTCGATGAGTGCTACATCCCCAATTACTTGCTCCCCAAAACCCAGCC
TGAGCTCCAATGGGCTTGGACCAACATGGAACAGTACTTGTCGGCCTGTTTGAATCTCACGGA
GCGTAAACGGTTGGTGGCGCAGCATCTGACGCACGTGTCGCAGACGCAGGAGCAGAACAAAGA
GAATCAGAATCCCAATTCTGATGCGCCGGTGATCAGATCAAAAACTTCAGCCAGGTACATGGA
GCTGGTCGGGTGGCTCGTGGACAAGGGGATTACCTCGGAGAAGCAGTGGATCCAGGAGGACCA
GGCCTCATACATCTCCTTCAATGCGGCCTCCAACTCGCGGTCCCAAATCAAGGCTGCCTTGGA
CAATGCGGGAAAGATTATGAGCCTGACTAAAACCGCCCCCGACTACCTGGTGGGCCAGCAGCC
CGTGGAGGACATTTCCAGCAATCGGATTTATAAAATTTTGGAACTAAACGGGTACGATCCCCA
ATATGCGGCTTCCGTCTTTCTGGGATGGGCCACGAAAAAGTTCGGCAAGAGGAACACCATCTG
GCTGTTTGGGCCTGCAACTACCGGGAAGACCAACATCGCGGAGGCCATAGCCCACACTGTGCC
CTTCTACGGGTGCGTAAACTGGACCAATGAGAACTTTCCCTTCAACGACTGTGTCGACAAGAT
GGTGATCTGGTGGGAGGAGGGGAAGATGACCGCCAAGGTCGTGGAGTCGGCCAAAGCCATTCT
CGGAGGAAGCAAGGTGCGCGTGGACCAGAAATGCAAGTCCTCGGCCCAGATAGACCCGACTCC
CGTGATCGTCACCTCCAACACCAACATGTGCGCCGTGATTGACGGGAACTCAACGACCTTCGA
ACACCAGCAGCCGTTGCAAGACCGGATGTTCAAATTTGAACTCACCCGCCGTCTGGATCATGA
CTTTGGGAAGGTCACCAAGCAGGAAGTCAAAGACTTTTTCCGGTGGGCAAAGGATCACGTGGT
TGAGGTGGAGCATGAATTCTACGTCAAAAAGGGTGGAGCCAAGAAAAGACCCGCCCCCAGTGA
CGCAGATATAAGTGAGCCCAAACGGGTGCGCGAGTCAGTTGCGCAGCCATCGACGTCAGACGC
GGAAGCTTCGATCAACTACGCAGACAGGTACCAAAACAAATGTTCTCGTCACGTGGGCATGAA
TCTGATGCTGTTTCCCTGCAGACAATGCGAGAGAATGAATCAGAATTCAAATATCTGCTTCAC
TCACGGACAGAAAGACTGTTTAGAGTGCTTTCCCGTGTCAGAATCTCAACCCGTTTCTGTCGT
CAAAAAGGCGTATCAGAAACTGTGCTACATTCATCATATCATGGGAAAGGTGCCAGACGCTTG
CACTGCCTGCGATCTGGTCAATGTGGATTTGGATGACTGCATCTTTGAACAATAAATGATTTA
AATCAGGTATGGCTGCCGATGGTTATCTTCCAGATTGGCTCGAGGACACTCTCTCTGAGTTAT
CATTTAAATGGCGCGCCCACGTGGGTACCGCGGCCGCGGGGATCCAGACATGATAAGATACAT
TGATGAGTTTGGACAAACCACAACTAGAATGCAGTGAAAAAAATGCTTTATTTGTGAAATTTG
TGATGCTATTGCTTTATTTGTAACCATTATAAGCTGCAATAAACAAGTTAACAACAACAATTG
CATTCATTTTATGTTTCAGGTTCAGGGGGAGGTGTGGGAGGTTTTTTCGGATCCTCTAGAGTC
GACCTGCAGGCA SEQ ID NO: 31
CMV forward primer
AAATGGCCCGCCTGGCATTATG SEQ ID NO: 32
CMV reverse primer
AAACCGCTATCCACGCCCATTG SEQ ID NO: 33
CMV probe
ACATGACCTTATGGGACTTTCCTACTTGGCAGTACATC SEQ ID NO: 34
AAV2 mutated p19 promoter region L (SP1 -50)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAATGGGCHTGGACTAATATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 35
AAV2 mutated p19 promoter region M (TATA -20)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACVAACATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG -continued SEQ ID NO: 36
AAV2 mutated p19 promoter region N (SP1 -50 1)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAATGGGCGTGGACTAATATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 37
AAV2 mutated p19 promoter region O (SP1 -50 2)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCHTGGACTAATATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 38
AAV2 mutated p19 promoter region P (TATA -20 1)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACVAATATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 39
AAV2 mutated p19 promoter region Q (TATA -20 2)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACTAACATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 40
AAV2 mutated p19 promoter region R (SP1 -50 & TATA -35)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAATGGGCHTGGACVAACATGGAA
CAGTATTTAAGCGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 41
AAV2 mutated p19 promoter region S (SP1 -50 & TATA -20)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAATGGGCHTGGACTAATATGGAA
CAGTACCTBTCDGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 42
AAV2 mutated p19 promoter region T (TATA -20 & TATA -35)
bold: regulatory sites within the p19 promoter
underlined: mutations in the p19 promoter region
CAGATTCGCGAAAAACTGATTCAGAGAATTTACCGCGGGATCGAGCCGACTTTGCCAAACTGG
TTCGCGGTCACAAAGACCAGAAATGGCGCCGGAGGCGGGAACAAGGTGGTGGATGAGTGCTAC
ATCCCCAATTACTTGCTCCCCAAAACCCAGCCTGAGCTCCAGTGGGCGTGGACVAACATGGAA -continued CAGTACCTBTCDGCCTGTTTGAATCTCACGGAGCGTAAACGGTTGGTGGCGCAGCATCTGACG
CACGTGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGGGATT
ACCTCGGAGAAGCAGTGGATCCAGG SEQ ID NO: 43
AAV2 Rep proteins coding region with mutated p19 promoter region L (SP-1)
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAATGGGCH
TGGACTAATATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 44
AAV2 Rep proteins coding region with mutated p19 promoter region M
(TATA -20) bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACVAACATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA -continued SEQ ID NO: 45
AAV2 Rep proteins coding region with mutated p19 promoter region N
(SP1 -50 1)
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAATGGGCG
TGGACTAATATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 46
AAV2 Rep proteins coding region with mutated p19 promoter region O
(SP1 -50 2)
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCH
TGGACTAATATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA -continued SEQ ID NO: 47
AAV2 Rep proteins coding region with mutated p19 promoter region P
(TATA -20 1)
bold: regulatory sites within the p19 promoter
underlined: mutations in the p19 promoter region ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACVAATATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 48
AAV2 Rep proteins coding region with mutated p19 promoter region Q
(TATA -202)
bold: regulatory sites within the p19 promoter
underlined: mutations in the p19 promoter region ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACTAACATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA -continued SEQ ID NO: 49
AAV2 Rep proteins coding region with mutated p19 promoter region R
(SP1 -50 & TATA -35)
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAATGGGCH
TGGACVAACATGGAACAGTATTTAAGCGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 50
AAV2 Rep proteins coding region with mutated p19 promoter region S
(SP1 -50 & TATA -20)
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAATGGGCH
TGGACTAATATGGAACAGTACCTBTCDGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA -continued SEQ ID NO: 51
AAV2 Rep proteins coding region with mutated p19 promoter region T
(TATA -20 & TATA -35)
bold: regulatory sites within the p19 promoter
underlined: mutations in the p19 promoter region
ATGCCGGGGTTTTACGAGATTGTGATTAAGGTCCCCAGCGACCTTGACGAGCATCTGCCCGGC
ATTTCTGACAGCTTTGTGAACTGGGTGGCCGAGAAGGAATGGGAGTTGCCGCCAGATTCTGAC
ATGGATCTGAATCTGATTGAGCAGGCACCCCTGACCGTGGCCGAGAAGCTGCAGCGCGACTTT
CTGACGGAATGGCGCCGTGTGAGTAAGGCCCCGGAGGCCCTTTTCTTTGTGCAATTTGAGAAG
GGAGAGAGCTACTTCCACATGCACGTGCTCGTGGAAACCACCGGGGTGAAATCCATGGTTTTG
GGACGTTTCCTGAGTCAGATTCGCGAAAAACTGATTCAGAGAATTTACCGCGGGATCGAGCCG
ACTTTGCCAAACTGGTTCGCGGTCACAAAGACCAGAAATGGCGCCGGAGGCGGGAACAAGGTG
GTGGATGAGTGCTACATCCCCAATTACTTGCTCCCCAAAACCCAGCCTGAGCTCCAGTGGGCG
TGGACVAACATGGAACAGTACCTBTCDGCCTGTTTGAATCTCACGGAGCGTAAACGGTTGGTG
GCGCAGCATCTGACGCACGTGTCGCAGACGCAGGAGCAGAACAAAGAGAATCAGAATCCCAAT
TCTGATGCGCCGGTGATCAGATCAAAAACTTCAGCCAGGTACATGGAGCTGGTCGGGTGGCTC
GTGGACAAGGGGATTACCTCGGAGAAGCAGTGGATCCAGGAGGACCAGGCCTCATACATCTCC
TTCAATGCGGCCTCCAACTCGCGGTCCCAAATCAAGGCTGCCTTGGACAATGCGGGAAAGATT
ATGAGCCTGACTAAAACCGCCCCCGACTACCTGGTGGGCCAGCAGCCCGTGGAGGACATTTCC
AGCAATCGGATTTATAAAATTTTGGAACTAAACGGGTACGATCCCCAATATGCGGCTTCCGTC
TTTCTGGGATGGGCCACGAAAAAGTTCGGCAAGAGGAACACCATCTGGCTGTTTGGGCCTGCA
ACTACCGGGAAGACCAACATCGCGGAGGCCATAGCCCACACTGTGCCCTTCTACGGGTGCGTA
AACTGGACCAATGAGAACTTTCCCTTCAACGACTGTGTCGACAAGATGGTGATCTGGTGGGAG
GAGGGGAAGATGACCGCCAAGGTCGTGGAGTCGGCCAAAGCCATTCTCGGAGGAAGCAAGGTG
CGCGTGGACCAGAAATGCAAGTCCTCGGCCCAGATAGACCCGACTCCCGTGATCGTCACCTCC
AACACCAACATGTGCGCCGTGATTGACGGGAACTCAACGACCTTCGAACACCAGCAGCCGTTG
CAAGACCGGATGTTCAAATTTGAACTCACCCGCCGTCTGGATCATGACTTTGGGAAGGTCACC
AAGCAGGAAGTCAAAGACTTTTTCCGGTGGGCAAAGGATCACGTGGTTGAGGTGGAGCATGAA
TTCTACGTCAAAAAGGGTGGAGCCAAGAAAAGACCCGCCCCCAGTGACGCAGATATAAGTGAG
CCCAAACGGGTGCGCGAGTCAGTTGCGCAGCCATCGACGTCAGACGCGGAAGCTTCGATCAAC
TACGCAGACAGGTACCAAAACAAATGTTCTCGTCACGTGGGCATGAATCTGATGCTGTTTCCC
TGCAGACAATGCGAGAGAATGAATCAGAATTCAAATATCTGCTTCACTCACGGACAGAAAGAC
TGTTTAGAGTGCTTTCCCGTGTCAGAATCTCAACCCGTTTCTGTCGTCAAAAAGGCGTATCAG
AAACTGTGCTACATTCATCATATCATGGGAAAGGTGCCAGACGCTTGCACTGCCTGCGATCTG
GTCAATGTGGATTTGGATGACTGCATCTTTGAACAATAAATGATTTAAATCAGGTATGGCTGC
CGATGGTTATCTTCCAGATTGGCTCGAGGACACTCTCTCTGA SEQ ID NO: 52
SV40 polvA forward primer
AGCAATAGCATCACAAATTTCACAA SEQ ID NO: 53
SV40 polvA reverse primer
CCAGACATGATAAGATACATTGATGAGTT SEQ ID NO: 54
SV40 polyA probe
AGCATTTTTTTCACTGCATTCTAGTTGTGGTTTGTC

The invention claimed is:

1. An isolated host cell comprising a nucleic acid encoding Adeno-associated virus (AAV) Rep proteins Rep78 and Rep68 operably linked to an inducible promoter, wherein the internal AAV promoter p19 comprises a substitution at position 818 from a guanine to an adenine wherein the position 818 is numbered according to a complete AAV2 genome of GenBank Accession number AF043303, whereby the internal AAV promoter p19 is inactivated and the functionality of said Rep78 and Rep68 proteins is maintained.

2. The isolated host cell according to claim 1, wherein said nucleic acid comprises SEQ ID NO: 36.

3. The isolated host cell according to claim 1, wherein said nucleic acid comprises SEQ ID NO: 45.

4. An isolated host cell, comprising a nucleic acid encoding Adeno-associated virus (AAV) Rep proteins Rep78 and Rep68 operably linked to an inducible promoter, wherein the internal AAV promoter p19 comprises a substitution at position 818 from a guanine to an adenine wherein the position 818 is numbered according to a complete AAV2 genome of GenBank Accession number AF043303, whereby the internal AAV promoter p19 is inactivated and the functionality of said Rep78 and said Rep68 proteins is maintained, wherein the nucleic acid also has at least 70% sequence identity to SEQ ID NO: 36.

5. The isolated host cell according to claim 1, wherein said nucleic acid is stably integrated into the host cell genome or is comprised in a vector.

6. The isolated host cell according to claim 1, further comprising a different nucleic acid encoding AAV Rep proteins Rep52 and Rep40 under the control of a heterologous, inducible promoter.

7. The isolated host cell according to claim 1, selected from the group consisting of CAP cells, HEK293 cells, and Per.C6 cells.

8. A nucleic acid encoding Adeno-associated virus (AAV) Rep proteins Rep78 and Rep68 operably linked to an inducible promoter, wherein the internal AAV promoter p19 comprises a substitution at position 818 from a guanine to an adenine wherein the position 818 is numbered according to a complete AAV2 genome of GenBank Accession number AF043303, whereby the internal AAV promoter p19 is has been inactivated by one or more mutations that maintain and the functionality of said Rep78 and Rep68 proteins is maintained.

9. A method for the production of Adeno-associated virus (AAV), comprising the step of recombinantly expressing an AAV vector genome along with MV Rep proteins Rep78 and Rep68 in the isolated host cell according to claim 1.

10. An isolated host cell, comprising a nucleic acid encoding Adeno-associated virus (AAV) Rep proteins Rep78 and Rep68 operably linked to an inducible promoter, wherein the internal AAV promoter p19 comprises a substitution at position 818 from a guanine to an adenine wherein the position 818 is numbered according to a complete AAV2 genome of GenBank Accession number AF043303, whereby the internal AAV promoter p19 is inactivated and the functionality of said Rep78 and said Rep68 proteins is maintained, wherein the nucleic acid also has at least 70% sequence identity to SEQ ID NO: 45.

* * * * *

SEQUENCE LISTING

<160> NUMBER OF SEQ ID NOS: 54

<210> SEQ ID NO 1
<211> LENGTH: 403
<212> TYPE: DNA
<213> ORGANISM: Artificial sequence
<220> FEATURE:
<223> OTHER INFORMATION: AAV mutated p19 promoter region mut19

<400> SEQUENCE: 1
cagattcgcg aaaaactgat tcagagaatt taccgcggga tcgagccgac tttgccaaac 60
tggttcgcgg tcacaaagac dcgbaacggc gccgggggbg ghaacaaagt hgthgatgag 120
tgctacatcc ccaattactt gctccccaaa acccagcctg agctccaatg ggchtggacv 180
aacatggaac agtacttgtc dgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

-continued

<210> SEQ ID NO 2
<211> LENGTH: 403
<212> TYPE: DNA
<213> ORGANISM: Artificial sequence
<220> FEATURE:
<223> OTHER INFORMATION: AAV mutated p19 promoter region mut5-1

<400> SEQUENCE: 2
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggcgtggact 180
aatatggaac agtacttgtc dgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 3
<211> LENGTH: 403
<212> TYPE: DNA
<213> ORGANISM: Artificial sequence
<220> FEATURE:
<223> OTHER INFORMATION: AAV mutated p19 promoter region mut1-1

<400> SEQUENCE: 3
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggcgtggact 180
aatatggaac agtatttgag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 4
<211> LENGTH: 403
<212> TYPE: DNA
<213> ORGANISM: Artificial sequence
<220> FEATURE:
<223> OTHER INFORMATION: AAV mutated p19 promoter region mut2-1

<400> SEQUENCE: 4
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggcgtggact 180
aatatggaac agtatttatc cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 5
<211> LENGTH: 403
<212> TYPE: DNA
<213> ORGANISM: Artificial sequence
<220> FEATURE:
<223> OTHER INFORMATION: AAV mutated p19 promoter region mut1-2

<400> SEQUENCE: 5

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggcgtggact    180

aatatggaac agtacttaag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 6
<211> LENGTH: 403
<212> TYPE: DNA
<213> ORGANISM: Artificial sequence
<220> FEATURE:
<223> OTHER INFORMATION: AAV mutated p19 promoter region mut14

<400> SEQUENCE: 6

```
cagattcgcg aaaaactgat tcagagaatt taccgcggga tcgagccgac tttgccaaac     60

tggttcgcgg tcacaaagac dcgbaacggc gccgggggbg ghaacaaagt hgthgatgag    120

tgctacatcc ccaattactt gctccccaaa acccagcctg agctccaatg ggchtggacv    180

aacatggaac agtatttaag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 7
<211> LENGTH: 403
<212> TYPE: DNA
<213> ORGANISM: Artificial sequence
<220> FEATURE:
<223> OTHER INFORMATION: AAV mutated p19 promoter region mut10-1

<400> SEQUENCE: 7

```
cagattcgcg aaaaactgat tcagagaatt taccgcggga tcgagccgac tttgccaaac     60

tggttcgcgg tcacaaagac acggaacggc gccgggggag gcaacaaagt cgtcgatgag    120

tgctacatcc ccaattactt gctccccaaa acccagcctg agctccagtg ggcgtggact    180

aatatggaac agtatttaag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 8
<211> LENGTH: 403
<212> TYPE: DNA
<213> ORGANISM: Artificial sequence
<220> FEATURE:
<223> OTHER INFORMATION: AAV mutated p19 promoter region mut10-2

<400> SEQUENCE: 8

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccaatg ggchtggacv    180
```

-continued

```
aacatggaac agtacctbtc dgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 9
<211> LENGTH: 403
<212> TYPE: DNA
<213> ORGANISM: Artificial sequence
<220> FEATURE:
<223> OTHER INFORMATION: AAV mutated p19 promoter region mut3

<400> SEQUENCE: 9

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggcgtggact    180

aatatggaac agtatgcbag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 10
<211> LENGTH: 403
<212> TYPE: DNA
<213> ORGANISM: Artificial sequence
<220> FEATURE:
<223> OTHER INFORMATION: AAV mutated p19 promoter region

<400> SEQUENCE: 10

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggghtggact    180

aatatggaac agtatttaag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 11
<211> LENGTH: 403
<212> TYPE: DNA
<213> ORGANISM: Artificial sequence
<220> FEATURE:
<223> OTHER INFORMATION: AAV mutated p19 promoter region

<400> SEQUENCE: 11

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggcgtggact    180

aatatggaac agtatctbag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

-continued

<210> SEQ ID NO 12
<211> LENGTH: 403
<212> TYPE: DNA
<213> ORGANISM: Artificial sequence
<220> FEATURE:
<223> OTHER INFORMATION: AAV mutated p19 promoter region mut1-3

<400> SEQUENCE: 12

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggcgtggact    180

aatatggaac agtatctaag cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 13
<211> LENGTH: 403
<212> TYPE: DNA
<213> ORGANISM: Artificial sequence
<220> FEATURE:
<223> OTHER INFORMATION: AAV mutated p19 promoter region mut5-2

<400> SEQUENCE: 13

```
cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggcgtggact    180

aatatggaac agtacctbtc cgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 14
<211> LENGTH: 403
<212> TYPE: DNA
<213> ORGANISM: Artificial sequence
<220> FEATURE:
<223> OTHER INFORMATION: AAV mutated p19 promoter region mut20

<400> SEQUENCE: 14

```
cagattcgcg aaaaactgat tcagagaatt taccgcggga tcgagccgac tttgccaaac     60

tggttcgcgg tcacaaagac dcgbaacggc gccgggggbg ghaacaaagt hgthgatgag    120

tgctacatcc ccaattactt gctccccaaa acccagcctg agctccaatg ggchtggacv    180

aacatggaac agtacctbtc dgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403
```

<210> SEQ ID NO 15
<211> LENGTH: 1932
<212> TYPE: DNA
<213> ORGANISM: Artificial sequence
<220> FEATURE:
<223> OTHER INFORMATION: AAV Rep proteins coding region with mutated p19
promoter region mut19

<400> SEQUENCE: 15

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac dcgbaacggc    420
gccgggggbg ghaacaaagt hgthgatgag tgctacatcc ccaattactt gctccccaaa    480
acccagcctg agctccaatg ggchtggacv aacatggaac agtacttgtc dgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 16
<211> LENGTH: 1932
<212> TYPE: DNA
<213> ORGANISM: Artificial sequence
<220> FEATURE:
<223> OTHER INFORMATION: AAV Rep proteins coding region with mutated p19
      promoter region mut5-1

<400> SEQUENCE: 16
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtacttgtc dgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 17
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut1-1

-continued

<400> SEQUENCE: 17

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttgag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 18
<211> LENGTH: 1932
<212> TYPE: DNA
<213> ORGANISM: Artificial sequence
<220> FEATURE:
<223> OTHER INFORMATION: AAV Rep proteins coding region with mutated p19
promoter region mut2-1

<400> SEQUENCE: 18
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatttatc cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 19
<211> LENGTH: 1932
<212> TYPE: DNA
<213> ORGANISM: Artificial sequence
<220> FEATURE:
<223> OTHER INFORMATION: AAV Rep proteins coding region with mutated p19
promoter region mut1-2

<400> SEQUENCE: 19

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtacttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 20
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut14

<400> SEQUENCE: 20

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac dcgbaacggc    420
gccgggggbg ghaacaaagt hgthgatgag tgctacatcc ccaattactt gctccccaaa    480
acccagcctg agctccaatg ggchtggacv aacatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 21
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut10-1

<400> SEQUENCE: 21

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac acggaacggc    420
gccgggggag gcaacaaagt cgtcgatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 22
<211> LENGTH: 1932
<212> TYPE: DNA
<213> ORGANISM: Artificial sequence
<220> FEATURE:
<223> OTHER INFORMATION: AAV Rep proteins coding region with mutated p19
promoter region mut10-2

<400> SEQUENCE: 22

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccaatg ggchtggacv aacatggaac agtacctbtc dgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 23
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut3

<400> SEQUENCE: 23

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatgcbag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                      1932
```

<210> SEQ ID NO 24
<211> LENGTH: 1932
<212> TYPE: DNA
<213> ORGANISM: Artificial sequence
<220> FEATURE:
<223> OTHER INFORMATION: AAV Rep proteins coding region with mutated p19
promoter region mut2-2

<400> SEQUENCE: 24
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggghtggact aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 25
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut2-3

<400> SEQUENCE: 25

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatctbag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 26
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut1-3

<400> SEQUENCE: 26
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtatctaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 27
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut5-2

-continued

<400> SEQUENCE: 27
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggact aatatggaac agtacctbtc cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 28
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region mut20

<400> SEQUENCE: 28

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatgg atctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac dcgbaacggc    420
gccgggggbg ghaacaaagt hgthgatgag tgctacatcc ccaattactt gctccccaaa    480
acccagcctg agctccaatg ggchtggacv aacatggaac agtacctbtc dgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataaatga tttaaatcag gtatggctgc cgatggttat cttccagatt ggctcgagga   1920
cactctctct ga                                                       1932
```

<210> SEQ ID NO 29
<211> LENGTH: 2184
<212> TYPE: DNA
<213> ORGANISM: Artificial sequence
<220> FEATURE:
<223> OTHER INFORMATION: synthetic AAV2 rep locus

<400> SEQUENCE: 29

```
gttaactgac gtgaattacg tcatagggtt agggaggtcc tgtattagag gtcacgtgag     60
tgttttgcga cattttgcga caccatgtgg tcacgctggg tatttaagcc cgagtgagca    120
cgcagggtct ccattttgaa gcgggaggtt tgaacgcgca gccgccatgc cggggtttta    180
cgagattgtg attaaggtcc ccagcgacct tgacgagcat ctgcccggca tttctgacag    240
ctttgtgaac tgggtggccg agaaggaatg ggagttgccg ccagattctg acatggatct    300
gaatctgatt gagcaggcac ccctgaccgt ggccgagaag ctgcagcgcg actttctgac    360
ggaatggcgc cgtgtgagta aggccccgga ggcccttttc tttgtgcaat ttgagaaggg    420
agagagctac ttccacatgc acgtgctcgt ggaaaccacc ggggtgaaat ccatggtttt    480
gggacgtttc ctgagtcaga ttcgcgaaaa actgattcag agaatttacc gcgggatcga    540
gccgactttg ccaaactggt tcgcggtcac aaagaccaga aatggcgccg gaggcgggaa    600
caaggtggtg gatgagtgct acatccccaa ttacttgctc cccaaaaccc agcctgagct    660
ccagtgggcg tggactaata tggaacagta tttaagcgcc tgtttgaatc tcacggagcg    720
taaacggttg gtggcgcagc atctgacgca cgtgtcgcag acgcaggagc agaacaaaga    780
gaatcagaat cccaattctg atgcgccggt gatcagatca aaaacttcag ccaggtacat    840
ggagctggtc gggtggctcg tggacaaggg gattacctcg gagaagcagt ggatccagga    900
ggaccaggcc tcatacatct ccttcaatgc ggcctccaac tcgcggtccc aaatcaaggc    960
tgccttggac aatgcgggaa agattatgag cctgactaaa accgcccccg actacctggt   1020
gggccagcag cccgtggagg acatttccag caatcggatt tataaaattt tggaactaaa   1080
cgggtacgat ccccaatatg cggcttccgt ctttctggga tgggccacga aaaagttcgg   1140
caagaggaac accatctggc tgtttgggcc tgcaactacc gggaagacca acatcgcgga   1200
ggccatagcc cacactgtgc ccttctacgg gtgcgtaaac tggaccaatg agaactttcc   1260
cttcaacgac tgtgtcgaca agatggtgat ctggtgggag gaggggaaga tgaccgccaa   1320
ggtcgtggag tcggccaaag ccattctcgg aggaagcaag gtgcgcgtgg accagaaatg   1380
caagtcctcg gcccagatag acccgactcc cgtgatcgtc acctccaaca ccaacatgtg   1440
cgccgtgatt gacgggaact caacgacctt cgaacaccag cagccgttgc aagaccggat   1500
gttcaaattt gaactcaccc gccgtctgga tcatgacttt gggaaggtca ccaagcagga   1560
agtcaaagac tttttccggt gggcaaagga tcacgtggtt gaggtggagc atgaattcta   1620
cgtcaaaaag ggtggagcca agaaaagacc cgcccccagt gacgcagata taagtgagcc   1680
caaacgggtg cgcgagtcag ttgcgcagcc atcgacgtca gacgcggaag cttcgatcaa   1740
ctacgcagac aggtaccaaa acaaatgttc tcgtcacgtg ggcatgaatc tgatgctgtt   1800
tccctgcaga caatgcgaga gaatgaatca gaattcaaat atctgcttca ctcacggaca   1860
gaaagactgt ttagagtgct ttcccgtgtc agaatctcaa cccgtttctg tcgtcaaaaa   1920
ggcgtatcag aaactgtgct acattcatca tatcatggga aaggtgccag acgcttgcac   1980
tgcctgcgat ctggtcaatg tggatttgga tgactgcatc tttgaacaat aaatgattta   2040
aatcaggtat ggctgccgat ggttatcttc cagattggct cgaggacact ctctctgaag   2100
gaataagaca gtggtggaag ctcaaacctg gcccaccacc accaaagccc gcagagcggc   2160
ataaggacga cagcaggggt taac                                          2184
```

```
<210> SEQ ID NO 30
<211> LENGTH: 4485
<212> TYPE: DNA
<213> ORGANISM: Artificial sequence
<220> FEATURE:
<223> OTHER INFORMATION: Inducible expression construct for AAV2 Rep
      proteins

<400> SEQUENCE: 30

gtttactccc tatcagtgat agagaacgta tgaagagttt actccctatc agtgatagag     60

aacgtatgca gactttactc cctatcagtg atagagaacg tataaggagt ttactcccta    120

tcagtgatag agaacgtatg accagtttac tccctatcag tgatagagaa cgtatctaca    180

gtttactccc tatcagtgat agagaacgta tatccagttt actccctatc agtgatagag    240

aacgtataag ctttaggcgt gtacggtggg cgcctataaa agcagagctc gtttagtgaa    300

ccgtcagatc gcctggagca attccacaac acttttgtct tataccaact ttccgtacca    360

cttcctaccc tcgtaaagtc gacaccgggg cccagatcta tcgatcggcc ggataacgcc    420

accatggagc tggtcgggtg gctcgtggac aaggggatta cctcggagaa gcagtggatc    480

caggaggacc aggcctcata catctccttc aatgcggcct ccaactcgcg gtcccaaatc    540

aaggctgcct tggacaatgc gggaaagatt atgagcctga ctaaaaccgc ccccgactac    600

ctggtgggcc agcagcccgt ggaggacatt tccagcaatc ggatttataa aattttggaa    660

ctaaacgggt acgatcccca atatgcggct tccgtctttc tgggatgggc cacgaaaaag    720

ttcggcaaga ggaacaccat ctggctgttt gggcctgcaa ctaccgggaa gaccaacatc    780

gcggaggcca tagcccacac tgtgcccttc tacgggtgcg taaactggac caatgagaac    840

tttcccttca acgactgtgt cgacaagatg gtgatctggt gggaggaggg gaagatgacc    900

gccaaggtcg tggagtcggc caaagccatt ctcggaggaa gcaaggtgcg cgtggaccag    960

aaatgcaagt cctcggccca gatagacccg actcccgtga tcgtcacctc caacaccaac   1020

atgtgcgccg tgattgacgg gaactcaacg accttcgaac accagcagcc gttgcaagac   1080

cggatgttca aatttgaact cacccgccgt ctggatcatg actttgggaa ggtcaccaag   1140

caggaagtca aagacttttt ccggtgggca aaggatcacg tggttgaggt ggagcatgaa   1200

ttctacgtca aaaagggtgg agccaagaaa agacccgccc ccagtgacgc agatataagt   1260

gagcccaaac gggtgcgcga gtcagttgcg cagccatcga cgtcagacgc ggaagcttcg   1320

atcaactacg cagacaggta ccaaaacaaa tgttctcgtc acgtgggcat gaatctgatg   1380

ctgtttccct gcagacaatg cgagagaatg aatcagaatt caaatatctg cttcactcac   1440

ggacagaaag actgtttaga gtgctttccc gtgtcagaat ctcaacccgt ttctgtcgtc   1500

aaaaaggcgt atcagaaact gtgctacatt catcatatca tgggaaaggt gccagacgct   1560

tgcactgcct gcgatctggt caatgtggat ttggatgact gcatctttga acaataaatg   1620

atttaaatca ggtatggctg ccgatggtta tcttccagat tggctcgagg acactctctc   1680

tgagataact gagggataga attccgcccc cccccctaa cgttactggc cgaagccgct    1740

tggaataagg ccggtgtgcg tttgtctata tgttattttc caccatattg ccgtcttttg   1800

gcaatgtgag ggcccggaaa cctggccctg tcttcttgac gagcattcct aggggtcttt   1860

cccctctcgc caaaggaatg caaggtctgt tgaatgtcgt gaaggaagca gttcctctgg   1920

aagcttcttg aagacaaaca acgtctgtag cgaccctttg caggcagcgg aaccccccac   1980

ctggcgacag gtgcctctgc ggccaaaagc cacgtgtata agatacacct gcaaaggcgg   2040

cacaacccca gtgccacgtt gtgagttgga tagttgtgga aagagtcaaa tggctctcct   2100
```

-continued

```
caagcgtatt caacaagggg ctgaaggatg cccagaaggt accccattgt atgggatctg   2160
atctggggcc tcggtgcaca tgctttacat gtgtttagtc gaggttaaaa aaacgtctag   2220
gccccccgaa ccacggggac gtggttttcc tttgaaaaac acgatgataa tagttatcgc   2280
cgccatgccg ggttttacg agattgtgat taaggtcccc agcgaccttg acgagcatct   2340
gcccggcatt tctgacagct ttgtgaactg ggtggccgag aaggaatggg agttgccgcc   2400
agattctgac atggatctga atctgattga gcaggcaccc ctgaccgtgg ccgagaagct   2460
gcagcgcgac tttctgacgg aatggcgccg tgtgagtaag gccccggagg cccttttctt   2520
tgtgcaattt gagaagggag agagctactt ccacatgcac gtgctcgtgg aaaccaccgg   2580
ggtgaaatcc atggttttgg gacgtttcct gagtcagatt cgcgaaaaac tgattcagag   2640
aatttaccgc gggatcgagc cgactttgcc aaactggttc gcggtcacaa agacacggaa   2700
cggcgccggg ggaggcaaca aagtcgtcga tgagtgctac atccccaatt acttgctccc   2760
caaaacccag cctgagctcc aatgggcttg gaccaacatg gaacagtact tgtcggcctg   2820
tttgaatctc acggagcgta aacggttggt ggcgcagcat ctgacgcacg tgtcgcagac   2880
gcaggagcag aacaaagaga atcagaatcc caattctgat gcgccggtga tcagatcaaa   2940
aacttcagcc aggtacatgg agctggtcgg gtggctcgtg gacaagggga ttacctcgga   3000
gaagcagtgg atccaggagg accaggcctc atacatctcc ttcaatgcgg cctccaactc   3060
gcggtcccaa atcaaggctg ccttggacaa tgcgggaaag attatgagcc tgactaaaac   3120
cgcccccgac tacctggtgg gccagcagcc cgtggaggac atttccagca atcggattta   3180
taaaattttg gaactaaacg ggtacgatcc ccaatatgcg gcttccgtct ttctgggatg   3240
ggccacgaaa aagttcggca agaggaacac catctggctg tttgggcctg caactaccgg   3300
gaagaccaac atcgcggagg ccatagccca cactgtgccc ttctacgggt gcgtaaactg   3360
gaccaatgag aactttccct tcaacgactg tgtcgacaag atggtgatct ggtgggagga   3420
ggggaagatg accgccaagg tcgtggagtc ggccaaagcc attctcggag gaagcaaggt   3480
gcgcgtggac cagaaatgca agtcctcggc ccagatagac ccgactcccg tgatcgtcac   3540
ctccaacacc aacatgtgcg ccgtgattga cgggaactca acgaccttcg aacaccagca   3600
gccgttgcaa gaccggatgt tcaaatttga actcacccgc cgtctggatc atgactttgg   3660
gaaggtcacc aagcaggaag tcaaagactt tttccggtgg gcaaaggatc acgtggttga   3720
ggtggagcat gaattctacg tcaaaaaggg tggagccaag aaaagacccg cccccagtga   3780
cgcagatata agtgagccca aacgggtgcg cgagtcagtt gcgcagccat cgacgtcaga   3840
cgcggaagct tcgatcaact acgcagacag gtaccaaaac aaatgttctc gtcacgtggg   3900
catgaatctg atgctgtttc cctgcagaca atgcgagaga atgaatcaga attcaaatat   3960
ctgcttcact cacggacaga aagactgttt agagtgcttt cccgtgtcag aatctcaacc   4020
cgtttctgtc gtcaaaaagg cgtatcagaa actgtgctac attcatcata tcatgggaaa   4080
ggtgccagac gcttgcactg cctgcgatct ggtcaatgtg gatttggatg actgcatctt   4140
tgaacaataa atgatttaaa tcaggtatgg ctgccgatgg ttatcttcca gattggctcg   4200
aggacactct ctctgagtta tcatttaaat ggcgcgccca cgtgggtacc gcggccgcgg   4260
ggatccagac atgataagat acattgatga gtttggacaa accacaacta gaatgcagtg   4320
aaaaaaatgc tttatttgtg aaatttgtga tgctattgct ttatttgtaa ccattataag   4380
ctgcaataaa caagttaaca acaacaattg cattcatttt atgtttcagg ttcaggggga   4440
ggtgtgggag gtttttcgg atcctctaga gtcgacctgc aggca                    4485
```

<210> SEQ ID NO 31
<211> LENGTH: 22
<212> TYPE: DNA
<213> ORGANISM: Artificial sequence
<220> FEATURE:
<223> OTHER INFORMATION: CMV forward primer

<400> SEQUENCE: 31
aaatggcccg cctggcatta tg 22

<210> SEQ ID NO 32
<211> LENGTH: 22
<212> TYPE: DNA
<213> ORGANISM: Artificial sequence
<220> FEATURE:
<223> OTHER INFORMATION: CMV reverse primer

<400> SEQUENCE: 32
aaaccgctat ccacgcccat tg 22

<210> SEQ ID NO 33
<211> LENGTH: 38
<212> TYPE: DNA
<213> ORGANISM: Artificial sequence
<220> FEATURE:
<223> OTHER INFORMATION: CMV probe

<400> SEQUENCE: 33
acatgacctt atgggacttt cctacttggc agtacatc 38

<210> SEQ ID NO 34
<211> LENGTH: 403
<212> TYPE: DNA
<213> ORGANISM: Artificial sequence
<220> FEATURE:
<223> OTHER INFORMATION: AAV mutated p19 promoter region L (SP1 -50)

<400> SEQUENCE: 34
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccaatg ggchtggact 180
aatatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 35
<211> LENGTH: 403
<212> TYPE: DNA
<213> ORGANISM: Artificial sequence
<220> FEATURE:
<223> OTHER INFORMATION: AAV mutated p19 promoter region M (TATA -20)

<400> SEQUENCE: 35
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggcgtggacv 180
aacatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 36
<211> LENGTH: 403
<212> TYPE: DNA
<213> ORGANISM: Artificial sequence
<220> FEATURE:
<223> OTHER INFORMATION: AAV mutated p19 promoter region N (SP1 -50 1)

<400> SEQUENCE: 36
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccaatg ggcgtggact 180
aatatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 37
<211> LENGTH: 403
<212> TYPE: DNA
<213> ORGANISM: Artificial sequence
<220> FEATURE:
<223> OTHER INFORMATION: AAV mutated p19 promoter region O (SP1 -50 2)

<400> SEQUENCE: 37
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggchtggact 180
aatatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 38
<211> LENGTH: 403
<212> TYPE: DNA
<213> ORGANISM: Artificial sequence
<220> FEATURE:
<223> OTHER INFORMATION: AAV mutated p19 promoter region P (TATA -20 1)

<400> SEQUENCE: 38
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggcgtggacv 180
aatatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 39
<211> LENGTH: 403
<212> TYPE: DNA
<213> ORGANISM: Artificial sequence
<220> FEATURE:
<223> OTHER INFORMATION: AAV mutated p19 promoter region Q (TATA -20 2)

<400> SEQUENCE: 39
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccagtg ggcgtggact 180
aacatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 40
<211> LENGTH: 403
<212> TYPE: DNA
<213> ORGANISM: Artificial sequence
<220> FEATURE:
<223> OTHER INFORMATION: AAV mutated p19 promoter region R (SP1 -50 & TATA -35)

<400> SEQUENCE: 40
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccaatg ggchtggacv 180
aacatggaac agtatttaag cgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 41
<211> LENGTH: 403
<212> TYPE: DNA
<213> ORGANISM: Artificial sequence
<220> FEATURE:
<223> OTHER INFORMATION: AAV mutated p19 promoter region S (SP1 -50 & TATA -20)

<400> SEQUENCE: 41
cagattcgcg aaaaactgat tcagagaatt taccgcggga tcgagccgac tttgccaaac 60
tggttcgcgg tcacaaagac cagaaatggc gccggaggcg ggaacaaggt ggtggatgag 120
tgctacatcc ccaattactt gctccccaaa acccagcctg agctccaatg ggchtggact 180
aatatggaac agtacctbtc dgcctgtttg aatctcacgg agcgtaaacg gttggtggcg 240
cagcatctga cgcacgtgtc gcagacgcag gagcagaaca aagagaatca gaatcccaat 300
tctgatgcgc cggtgatcag atcaaaaact tcagccaggt acatggagct ggtcgggtgg 360
ctcgtggaca aggggattac ctcggagaag cagtggatcc agg 403

<210> SEQ ID NO 42
<211> LENGTH: 403
<212> TYPE: DNA
<213> ORGANISM: Artificial sequence -continued

```
<220> FEATURE:
<223> OTHER INFORMATION: AAV mutated p19 promoter region T (TATA -20 &
      TATA -35)

<400> SEQUENCE: 42

cagattcgcg aaaaactgat tcagagaatt taccgcggga tcgagccgac tttgccaaac     60

tggttcgcgg tcacaaagac cagaaatggc gccggaggcg ggaacaaggt ggtggatgag    120

tgctacatcc ccaattactt gctccccaaa acccagcctg agctccagtg ggcgtggacv    180

aacatggaac agtacctbtc dgcctgtttg aatctcacgg agcgtaaacg gttggtggcg    240

cagcatctga cgcacgtgtc gcagacgcag gagcagaaca aagagaatca gaatcccaat    300

tctgatgcgc cggtgatcag atcaaaaact tcagccaggt acatggagct ggtcgggtgg    360

ctcgtggaca aggggattac ctcggagaag cagtggatcc agg                      403


<210> SEQ ID NO 43
<211> LENGTH: 1932
<212> TYPE: DNA
<213> ORGANISM: Artificial sequence
<220> FEATURE:
<223> OTHER INFORMATION: AAV Rep proteins coding region with mutated p19
      promoter region L (SP1 -50)

<400> SEQUENCE: 43

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccaatg ggchtggact aatatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440
```

```
gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                       1932
```

<210> SEQ ID NO 44
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region M (TATA -20)

<400> SEQUENCE: 44

```
atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccagtg ggcgtggacv aacatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500
```

-continued

```
gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                       1932
```

```
<210> SEQ ID NO 45
<211> LENGTH: 1932
<212> TYPE: DNA
<213> ORGANISM: Artificial sequence
<220> FEATURE:
<223> OTHER INFORMATION: AAV Rep proteins coding region with mutated p19
      promoter region N (SP1 -50 1)

<400> SEQUENCE: 45

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccaatg ggcgtggact aatatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560
```

-continued

```
gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                       1932


<210> SEQ ID NO 46
<211> LENGTH: 1932
<212> TYPE: DNA
<213> ORGANISM: Artificial sequence
<220> FEATURE:
<223> OTHER INFORMATION: AAV Rep proteins coding region with mutated p19
      promoter region O (SP1 -50 2)

<400> SEQUENCE: 46

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccagtg ggchtggact aatatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620
```

aatctgatgc tgtttccctg cagacaatgc gagagaatga atcagaattc aaatatctgc 1680
ttcactcacg gacagaaaga ctgtttagag tgctttcccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
cactctctct ga 1932

<210> SEQ ID NO 47
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region P (TATA -20 1)

<400> SEQUENCE: 47
atgccggggt tttacgagat tgtgattaag gtccccagcg accttgacga gcatctgccc 60
ggcatttctg acagctttgt gaactgggtg gccgagaagg aatgggagtt gccgccagat 120
tctgacatgg atctgaatct gattgagcag gcacccctga ccgtggccga gaagctgcag 180
cgcgactttc tgacggaatg gcgccgtgtg agtaaggccc cggaggccct tttctttgtg 240
caatttgaga agggagagag ctacttccac atgcacgtgc tcgtggaaac caccggggtg 300
aaatccatgg ttttgggacg tttcctgagt cagattcgcg aaaaactgat tcagagaatt 360
taccgcggga tcgagccgac tttgccaaac tggttcgcgg tcacaaagac cagaaatggc 420
gccggaggcg ggaacaaggt ggtggatgag tgctacatcc ccaattactt gctccccaaa 480
acccagcctg agctccagtg ggcgtggacv aatatggaac agtatttaag cgcctgtttg 540
aatctcacgg agcgtaaacg gttggtggcg cagcatctga cgcacgtgtc gcagacgcag 600
gagcagaaca aagagaatca gaatcccaat tctgatgcgc cggtgatcag atcaaaaact 660
tcagccaggt acatggagct ggtcgggtgg ctcgtggaca aggggattac ctcggagaag 720
cagtggatcc aggaggacca ggcctcatac atctccttca atgcggcctc caactcgcgg 780
tcccaaatca aggctgcctt ggacaatgcg ggaaagatta tgagcctgac taaaaccgcc 840
cccgactacc tggtgggcca gcagcccgtg gaggacattt ccagcaatcg gatttataaa 900
attttggaac taaacgggta cgatccccaa tatgcggctt ccgtctttct gggatgggcc 960
acgaaaaagt tcggcaagag gaacaccatc tggctgtttg ggcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agactttttc cggtgggcaa aggatcacgt ggttgaggtg 1440
gagcatgaat tctacgtcaa aaagggtgga gccaagaaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680

-continued

```
ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                       1932
```

<210> SEQ ID NO 48
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region Q (TATA -20 2)

<400> SEQUENCE: 48

```
atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccagtg ggcgtggact aacatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740
```

```
tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                       1932
```

<210> SEQ ID NO 49
<211> LENGTH: 1932
<212> TYPE: DNA
<213> ORGANISM: Artificial sequence
<220> FEATURE:
<223> OTHER INFORMATION: AAV Rep proteins coding region with mutated p19 promoter region R (SP1 -50 & TATA -35)

<400> SEQUENCE: 49

```
atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccaatg ggchtggacv aacatggaac agtatttaag cgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800
```

```
ccagacgctt gcactgcctg cgatctggtc aatgtggatt tggatgactg catctttgaa   1860

caataaatga tttaaatcag gtatggctgc cgatggttat cttccagatt ggctcgagga   1920

cactctctct ga                                                        1932


<210> SEQ ID NO 50
<211> LENGTH: 1932
<212> TYPE: DNA
<213> ORGANISM: Artificial sequence
<220> FEATURE:
<223> OTHER INFORMATION: AAV Rep proteins coding region with mutated p19
      promoter region S (SP1 -50 & TATA -20)

<400> SEQUENCE: 50

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccaatg ggchtggact aatatggaac agtacctbtc dgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860
```

```
caataaatga tttaaatcag gtatggctgc cgatggttat cttccagatt ggctcgagga   1920

cactctctct ga                                                        1932


<210> SEQ ID NO 51
<211> LENGTH: 1932
<212> TYPE: DNA
<213> ORGANISM: Artificial sequence
<220> FEATURE:
<223> OTHER INFORMATION: AAR Rep proteins coding region with mutated p19
      promoter region T (TATA -20 & TATA -35)

<400> SEQUENCE: 51

atgccggggt tttacgagat tgtgattaag gtccccagcg accttgacga gcatctgccc     60

ggcatttctg acagctttgt gaactgggtg gccgagaagg aatgggagtt gccgccagat    120

tctgacatgg atctgaatct gattgagcag gcacccctga ccgtggccga gaagctgcag    180

cgcgactttc tgacggaatg gcgccgtgtg agtaaggccc cggaggccct tttctttgtg    240

caatttgaga agggagagag ctacttccac atgcacgtgc tcgtggaaac caccggggtg    300

aaatccatgg ttttgggacg tttcctgagt cagattcgcg aaaaactgat tcagagaatt    360

taccgcggga tcgagccgac tttgccaaac tggttcgcgg tcacaaagac cagaaatggc    420

gccggaggcg ggaacaaggt ggtggatgag tgctacatcc ccaattactt gctccccaaa    480

acccagcctg agctccagtg ggcgtggacv aacatggaac agtacctbtc dgcctgtttg    540

aatctcacgg agcgtaaacg gttggtggcg cagcatctga cgcacgtgtc gcagacgcag    600

gagcagaaca aagagaatca gaatcccaat tctgatgcgc cggtgatcag atcaaaaact    660

tcagccaggt acatggagct ggtcgggtgg ctcgtggaca aggggattac ctcggagaag    720

cagtggatcc aggaggacca ggcctcatac atctccttca atgcggcctc caactcgcgg    780

tcccaaatca aggctgcctt ggacaatgcg ggaaagatta tgagcctgac taaaaccgcc    840

cccgactacc tggtgggcca gcagcccgtg gaggacattt ccagcaatcg gatttataaa    900

attttggaac taaacgggta cgatccccaa tatgcggctt ccgtctttct gggatgggcc    960

acgaaaaagt tcggcaagag gaacaccatc tggctgtttg ggcctgcaac taccgggaag   1020

accaacatcg cggaggccat agcccacact gtgcccttct acgggtgcgt aaactggacc   1080

aatgagaact ttcccttcaa cgactgtgtc gacaagatgg tgatctggtg ggaggagggg   1140

aagatgaccg ccaaggtcgt ggagtcggcc aaagccattc tcggaggaag caaggtgcgc   1200

gtggaccaga aatgcaagtc ctcggcccag atagacccga ctcccgtgat cgtcacctcc   1260

aacaccaaca tgtgcgccgt gattgacggg aactcaacga ccttcgaaca ccagcagccg   1320

ttgcaagacc ggatgttcaa atttgaactc acccgccgtc tggatcatga ctttgggaag   1380

gtcaccaagc aggaagtcaa agactttttc cggtgggcaa aggatcacgt ggttgaggtg   1440

gagcatgaat tctacgtcaa aaagggtgga gccaagaaaa gacccgcccc cagtgacgca   1500

gatataagtg agcccaaacg ggtgcgcgag tcagttgcgc agccatcgac gtcagacgcg   1560

gaagcttcga tcaactacgc agacaggtac caaaacaaat gttctcgtca cgtgggcatg   1620

aatctgatgc tgtttccctg cagacaatgc gagagaatga atcagaattc aaatatctgc   1680

ttcactcacg gacagaaaga ctgtttagag tgctttcccg tgtcagaatc tcaacccgtt   1740

tctgtcgtca aaaaggcgta tcagaaactg tgctacattc atcatatcat gggaaaggtg   1800

ccagacgctt gcactgcctg cgatctggtc aatgtggatt tggatgactg catctttgaa   1860
```

-continued

```
caataaatga tttaaatcag gtatggctgc cgatggttat cttccagatt ggctcgagga   1920

cactctctct ga                                                       1932


<210> SEQ ID NO 52
<211> LENGTH: 25
<212> TYPE: DNA
<213> ORGANISM: Artificial sequence
<220> FEATURE:
<223> OTHER INFORMATION: SV40 poly A forward primer

<400> SEQUENCE: 52

agcaatagca tcacaaattt cacaa                                           25


<210> SEQ ID NO 53
<211> LENGTH: 29
<212> TYPE: DNA
<213> ORGANISM: Artificial sequence
<220> FEATURE:
<223> OTHER INFORMATION: SV40 poly A reverse primer

<400> SEQUENCE: 53

ccagacatga taagatacat tgatgagtt                                       29


<210> SEQ ID NO 54
<211> LENGTH: 36
<212> TYPE: DNA
<213> ORGANISM: Artificial sequence
<220> FEATURE:
<223> OTHER INFORMATION: SV40 poly A probe

<400> SEQUENCE: 54

agcatttttt tcactgcatt ctagttgtgg tttgtc                               36
```